(12) United States Patent
Worden et al.

(10) Patent No.: US 9,746,452 B2
(45) Date of Patent: Aug. 29, 2017

(54) WIRELESS SYSTEM AND METHOD FOR MEASURING AN OPERATIVE CONDITION OF A MACHINE

(71) Applicant: GENERAL ELECTRIC COMPANY, Schenectady, NY (US)

(72) Inventors: Bret Dwayne Worden, Laurence, PA (US); Mahalakshmi Shunmugham Balasubramaniam, Bangalore (IN); Ajith Kuttannair Kumar, Lawrence Park, PA (US); Jingjun Zhang, Lawrence Park, PA (US); Jennifer Lynn Coyne, Lawrence Park, PA (US); Sachidananda Chinagudi Jagadeesha, Bangalore (IN)

(73) Assignee: General Electric Company, Schenectady, NY (US)

( * ) Notice: Subject to any disclaimer, the term of this patent is extended or adjusted under 35 U.S.C. 154(b) by 6 days.

(21) Appl. No.: 14/421,245

(22) PCT Filed: Aug. 21, 2013

(86) PCT No.: PCT/US2013/055983
§ 371 (c)(1),
(2) Date: Feb. 12, 2015

(87) PCT Pub. No.: WO2014/031749
PCT Pub. Date: Feb. 27, 2014

(65) Prior Publication Data
US 2015/0198578 A1    Jul. 16, 2015

Related U.S. Application Data

(60) Provisional application No. 61/692,230, filed on Aug. 22, 2012.

(51) Int. Cl.
*G01N 33/26* (2006.01)
*F16N 29/00* (2006.01)
*G01M 13/02* (2006.01)

(52) U.S. Cl.
CPC .............. *G01N 33/26* (2013.01); *F16N 29/00* (2013.01); *G01M 13/02* (2013.01)

(58) Field of Classification Search
CPC ......... G01N 33/26; F16N 29/00; G01M 13/02
(Continued)

(56) References Cited

U.S. PATENT DOCUMENTS

| 3,675,121 A | 7/1972 | Thompson |
| 3,778,706 A | 12/1973 | Thompson |

(Continued)

FOREIGN PATENT DOCUMENTS

| CN | 1363844 A | 8/2002 |
| CN | 1532372 A | 9/2004 |

(Continued)

OTHER PUBLICATIONS

Macdiarmid, "Synthetic Metals: A Novel Role for Organic Polymers", Angewandte Chemie International Edition, vol. No. 40, pp. 2581-2590, 2001.

(Continued)

*Primary Examiner* — Peter Macchiarolo
*Assistant Examiner* — Nathaniel Kolb
(74) *Attorney, Agent, or Firm* — Global Patent Operation; John A. Kramer

(57) ABSTRACT

System including a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system also includes a device body (Continued)

operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

19 Claims, 9 Drawing Sheets

(58) Field of Classification Search
USPC .................. 73/290 R–334, 290 B, 290 V
See application file for complete search history.

(56) References Cited

U.S. PATENT DOCUMENTS

| | | |
|---|---|---|
| 3,927,369 A | 12/1975 | Billeter et al. |
| 4,096,385 A | 6/1978 | Marett |
| 4,273,636 A | 6/1981 | Shimada et al. |
| 4,275,364 A | 6/1981 | Skatvold |
| 4,372,164 A | 2/1983 | Brown et al. |
| 4,553,434 A | 11/1985 | Spaargaren |
| 4,728,892 A | 3/1988 | Vinegar et al. |
| 4,820,989 A | 4/1989 | Vail, III |
| 4,844,097 A | 7/1989 | Bellhouse et al. |
| 4,876,512 A | 10/1989 | Kroeger et al. |
| 4,882,542 A | 11/1989 | Vail, III |
| 4,887,455 A | 12/1989 | Payne et al. |
| 4,887,798 A | 12/1989 | Julius |
| 4,922,745 A | 5/1990 | Rudkin et al. |
| 4,941,958 A | 7/1990 | Byers |
| 4,965,522 A | 10/1990 | Hazen et al. |
| 4,996,490 A | 2/1991 | Scott et al. |
| 5,010,301 A | 4/1991 | Leung et al. |
| 5,025,346 A | 6/1991 | Tang et al. |
| 5,059,790 A | 10/1991 | Klainer et al. |
| 5,089,780 A | 2/1992 | Megerle |
| 5,157,338 A | 10/1992 | Motherbaugh et al. |
| 5,208,165 A | 5/1993 | Law et al. |
| 5,241,364 A | 8/1993 | Kimura |
| 5,260,569 A | 11/1993 | Kimura |
| 5,306,644 A | 4/1994 | Myerholtz et al. |
| 5,344,547 A | 9/1994 | Vlasov et al. |
| 5,421,983 A | 6/1995 | Slack et al. |
| 5,443,985 A | 8/1995 | Lu et al. |
| 5,497,140 A | 3/1996 | Tuttle |
| 5,543,722 A | 8/1996 | Suzuki et al. |
| 5,591,896 A | 1/1997 | Lin |
| 5,592,040 A | 1/1997 | Yamamoto |
| 5,607,566 A | 3/1997 | Brown et al. |
| 5,646,592 A | 7/1997 | Tuttle |
| 5,672,319 A | 9/1997 | Eisum |
| 5,744,902 A | 4/1998 | Vig |
| 5,751,475 A | 5/1998 | Ishiwata et al. |
| 5,754,055 A | 5/1998 | McAdoo et al. |
| 5,785,181 A | 7/1998 | Quartararo, Jr. |
| 5,786,595 A | 7/1998 | Herron et al. |
| 5,817,943 A | 10/1998 | Welles, II et al. |
| 5,831,439 A | 11/1998 | Suenram et al. |
| 5,840,168 A | 11/1998 | Chaniotakis et al. |
| 5,874,047 A | 2/1999 | Schoening et al. |
| 5,961,923 A | 10/1999 | Nova et al. |
| 6,025,725 A | 2/2000 | Gershenfeld et al. |
| 6,025,783 A | 2/2000 | Steffens, Jr. |
| 6,111,520 A | 8/2000 | Allen et al. |
| 6,166,546 A | 12/2000 | Scheihing et al. |
| 6,189,656 B1 | 2/2001 | Morgenstern et al. |
| 6,192,753 B1 | 2/2001 | Czarnek |
| 6,204,764 B1 | 3/2001 | Maloney |
| 6,278,379 B1 | 8/2001 | Allen et al. |
| 6,287,765 B1 | 9/2001 | Cubicciotti |
| 6,359,444 B1 | 3/2002 | Grimes |
| 6,360,585 B1 | 3/2002 | Potyrailo et al. |
| 6,398,931 B1 | 6/2002 | Burchette et al. |
| 6,399,375 B2 | 6/2002 | Vajta |
| 6,406,668 B1 | 6/2002 | Dordick et al. |
| 6,461,872 B1 | 10/2002 | Sivavec et al. |
| 6,471,838 B1 | 10/2002 | Igel et al. |
| 6,506,346 B1 | 1/2003 | Monro |
| 6,532,834 B1 | 3/2003 | Pinto et al. |
| 6,544,193 B2 | 4/2003 | Abreu |
| 6,586,946 B2 | 7/2003 | Hefti et al. |
| 6,614,229 B1 | 9/2003 | Clark et al. |
| 6,657,429 B1 | 12/2003 | Goldfine et al. |
| 6,672,512 B2 | 1/2004 | Bridgelall |
| 6,676,903 B2 | 1/2004 | Potyrailo et al. |
| 6,730,201 B1 | 5/2004 | Kuhlman et al. |
| 6,751,557 B1 | 6/2004 | Shehab et al. |
| 6,771,074 B2 | 8/2004 | Zou et al. |
| 6,773,926 B1 | 8/2004 | Freund et al. |
| 6,780,307 B2 | 8/2004 | Kidwell |
| 6,782,736 B1 | 8/2004 | Hammer |
| 6,804,544 B2 | 10/2004 | Van Antwerp et al. |
| 6,818,450 B2 | 11/2004 | Eaton et al. |
| 6,864,801 B2 | 3/2005 | Tabanou et al. |
| 6,891,383 B2 | 5/2005 | Nicholson et al. |
| 6,911,818 B2 | 6/2005 | Julius |
| 6,953,520 B2 | 10/2005 | Yengoyan et al. |
| 7,017,404 B1 | 3/2006 | Kain |
| 7,031,560 B2 | 4/2006 | Lelong-Feneyrou et al. |
| 7,034,660 B2 | 4/2006 | Watters et al. |
| 7,038,470 B1 | 5/2006 | Johnson |
| 7,040,139 B2 | 5/2006 | Sunshine |
| 7,076,858 B2 | 7/2006 | Eckstein et al. |
| 7,113,125 B2 | 9/2006 | Le Sesne |
| 7,125,382 B2 | 10/2006 | Zhou et al. |
| 7,126,013 B2 | 10/2006 | Heeney et al. |
| 7,168,310 B2 | 1/2007 | Al-Ruwaili |
| 7,171,312 B2 | 1/2007 | Steinthal et al. |
| 7,178,416 B2 | 2/2007 | Whelan et al. |
| 7,204,128 B1 | 4/2007 | Liu et al. |
| 7,252,010 B2 | 8/2007 | Ohta et al. |
| 7,276,916 B2 | 10/2007 | Hammer |
| 7,293,450 B2 | 11/2007 | Liu et al. |
| 7,317,989 B2 | 1/2008 | DiFoggio et al. |
| 7,335,336 B1 | 2/2008 | Kim |
| 7,343,800 B2 * | 3/2008 | Harman .................. G01F 23/68 73/313 |
| 7,350,367 B2 | 4/2008 | Matsiev et al. |
| 7,434,457 B2 | 10/2008 | Goodwin et al. |
| 7,445,143 B2 | 11/2008 | Pang et al. |
| 7,449,893 B1 | 11/2008 | Tsironis |
| 7,455,108 B2 | 11/2008 | Jenkins et al. |
| 7,456,744 B2 | 11/2008 | Kuhns |
| 7,466,041 B2 | 12/2008 | Urman |
| 7,481,771 B2 | 1/2009 | Fonseca et al. |
| 7,483,743 B2 | 1/2009 | Mann et al. |
| 7,486,495 B1 | 2/2009 | Diederichs et al. |
| 7,495,454 B2 | 2/2009 | Rivera |
| 7,523,647 B2 | 4/2009 | Scott |
| 7,562,557 B2 | 7/2009 | Bennett et al. |
| 7,569,810 B1 | 8/2009 | Troxler et al. |
| 7,629,167 B2 | 12/2009 | Hodge et al. |
| 7,677,307 B2 | 3/2010 | Vasques et al. |
| 7,691,329 B2 | 4/2010 | Potyrailo et al. |
| 7,697,574 B2 | 4/2010 | Suematsu et al. |
| 7,808,235 B2 | 10/2010 | Rollins et al. |
| 7,812,609 B2 | 10/2010 | Martinez et al. |
| 7,814,786 B2 * | 10/2010 | Woodard ............ G01R 33/1223 73/291 |
| 7,911,345 B2 | 3/2011 | Potyrailo et al. |
| 7,948,380 B2 | 5/2011 | Kuhns et al. |
| 7,948,385 B2 | 5/2011 | Potyrailo et al. |
| 7,958,772 B2 | 6/2011 | Permuy et al. |
| 7,969,307 B2 | 6/2011 | Peeters |
| 8,018,342 B2 | 9/2011 | Monk et al. |
| 8,063,648 B2 | 11/2011 | Nilsson et al. |
| 8,111,143 B2 | 2/2012 | Tong et al. |
| 8,154,389 B2 | 4/2012 | Rowland et al. |
| 8,155,891 B2 | 4/2012 | Kong et al. |
| 8,159,347 B2 | 4/2012 | Potyrailo et al. |
| 8,184,290 B2 | 5/2012 | Hertens et al. |
| 8,190,394 B2 | 5/2012 | Davis et al. |

(56) References Cited

U.S. PATENT DOCUMENTS

| | | | |
|---|---|---|---|
| 8,215,166 B2* | 7/2012 | Cunningham | E03F 5/16 73/304 C |
| 8,232,091 B2 | 7/2012 | Maltezos et al. | |
| 8,246,910 B2 | 8/2012 | Dhirani et al. | |
| 8,261,618 B2 | 9/2012 | Engle et al. | |
| 8,318,099 B2 | 11/2012 | Potyrailo et al. | |
| 8,342,242 B2 | 1/2013 | Roddy et al. | |
| 8,429,985 B2 | 4/2013 | Furlong | |
| 8,452,716 B2 | 5/2013 | Howley et al. | |
| 8,468,871 B2 | 6/2013 | Potyrailo et al. | |
| 8,508,368 B2 | 8/2013 | Potyrailo et al. | |
| 8,547,110 B2 | 10/2013 | Kesil et al. | |
| 8,643,388 B2 | 2/2014 | Hedges | |
| 8,676,436 B2 | 3/2014 | Raimarckers et al. | |
| 8,710,973 B2 | 4/2014 | Schneider et al. | |
| 8,732,938 B2 | 5/2014 | Kolosov et al. | |
| 8,736,425 B2 | 5/2014 | Potyrailo | |
| 8,833,145 B2 | 9/2014 | Fischer et al. | |
| 8,933,706 B1 | 1/2015 | Karlquist | |
| 8,952,708 B2 | 2/2015 | Nikolenko | |
| 9,074,966 B2 | 7/2015 | Sanderlin et al. | |
| 2001/0045355 A1 | 11/2001 | Gephart et al. | |
| 2002/0050929 A1 | 5/2002 | Parrotta et al. | |
| 2002/0081231 A1 | 6/2002 | Shapiro et al. | |
| 2002/0089356 A1 | 7/2002 | Perrott et al. | |
| 2002/0149466 A1 | 10/2002 | Sunshine et al. | |
| 2002/0173040 A1 | 11/2002 | Potyrailo et al. | |
| 2002/0177232 A1 | 11/2002 | Melker et al. | |
| 2002/0197725 A1 | 12/2002 | Eaton et al. | |
| 2003/0053936 A1 | 3/2003 | Potyrailo et al. | |
| 2003/0154031 A1 | 8/2003 | Potyrailo et al. | |
| 2003/0179024 A1 | 9/2003 | Montagnana | |
| 2003/0232223 A1 | 12/2003 | Leddy et al. | |
| 2004/0051154 A1 | 3/2004 | Yamakawa et al. | |
| 2004/0113790 A1 | 6/2004 | Hamel et al. | |
| 2004/0125442 A1 | 7/2004 | Yun et al. | |
| 2004/0155667 A1 | 8/2004 | Kesil et al. | |
| 2004/0189487 A1 | 9/2004 | Hoefel et al. | |
| 2004/0219523 A1 | 11/2004 | Stanton et al. | |
| 2004/0227682 A1 | 11/2004 | Anderson | |
| 2004/0248315 A1 | 12/2004 | Klein et al. | |
| 2005/0022581 A1 | 2/2005 | Sunshine | |
| 2005/0058460 A1 | 3/2005 | Wang | |
| 2005/0093760 A1 | 5/2005 | Rochelle et al. | |
| 2005/0161405 A1 | 7/2005 | Holland | |
| 2005/0193832 A1 | 9/2005 | Tombs et al. | |
| 2005/0199731 A9 | 9/2005 | Empedocles et al. | |
| 2006/0014172 A1 | 1/2006 | Muller et al. | |
| 2006/0020427 A1 | 1/2006 | Kahn et al. | |
| 2006/0055531 A1 | 3/2006 | Cook et al. | |
| 2006/0081471 A1 | 4/2006 | Kidwell | |
| 2006/0133720 A1 | 6/2006 | Hochberg et al. | |
| 2006/0141469 A1 | 6/2006 | Rossier et al. | |
| 2006/0198760 A1 | 9/2006 | Potyrailo et al. | |
| 2006/0205093 A1 | 9/2006 | Prins | |
| 2006/0210440 A1 | 9/2006 | Potyrailo et al. | |
| 2006/0238349 A1 | 10/2006 | Hu et al. | |
| 2006/0265150 A1 | 11/2006 | Hu et al. | |
| 2007/0029195 A1 | 2/2007 | Li et al. | |
| 2007/0064839 A1 | 3/2007 | Luu | |
| 2007/0084277 A1 | 4/2007 | Steinsiek | |
| 2007/0085686 A1 | 4/2007 | Oz | |
| 2007/0090926 A1 | 4/2007 | Potyrailo et al. | |
| 2007/0111222 A1 | 5/2007 | Chasin et al. | |
| 2007/0131418 A1 | 6/2007 | Barrow et al. | |
| 2007/0148670 A1 | 6/2007 | O'Malley | |
| 2007/0176773 A1 | 8/2007 | Smolander et al. | |
| 2007/0186648 A1* | 8/2007 | Harmon | G01F 23/72 73/319 |
| 2007/0236338 A1 | 10/2007 | Maruyama | |
| 2007/0241890 A1 | 10/2007 | Yoshioka | |
| 2008/0090926 A1 | 4/2008 | Kang et al. | |
| 2008/0093219 A1 | 4/2008 | Goldberg et al. | |
| 2008/0116908 A1 | 5/2008 | Potyrailo et al. | |
| 2008/0135614 A1 | 6/2008 | Werner et al. | |
| 2008/0142366 A1 | 6/2008 | Tamirisa et al. | |
| 2008/0157901 A1 | 7/2008 | Matekovits et al. | |
| 2008/0177150 A1 | 7/2008 | Ii et al. | |
| 2008/0179197 A1 | 7/2008 | Wu | |
| 2008/0180249 A1 | 7/2008 | Butler et al. | |
| 2008/0184787 A1 | 8/2008 | Coates | |
| 2008/0184795 A1* | 8/2008 | Woodard | G01R 33/1223 73/304 C |
| 2008/0191859 A1 | 8/2008 | Tiek et al. | |
| 2008/0236814 A1 | 10/2008 | Roddy | |
| 2008/0280374 A1 | 11/2008 | Potyrailo et al. | |
| 2009/0035856 A1 | 2/2009 | Galliher et al. | |
| 2009/0039864 A1 | 2/2009 | Gordon | |
| 2009/0087862 A1 | 4/2009 | Carter et al. | |
| 2009/0095073 A1 | 4/2009 | Fukumura et al. | |
| 2009/0104073 A1 | 4/2009 | Wang et al. | |
| 2009/0120169 A1 | 5/2009 | Chandler et al. | |
| 2009/0139325 A1* | 6/2009 | Cunningham | G01F 23/268 73/304 C |
| 2009/0204250 A1 | 8/2009 | Potyrailo et al. | |
| 2009/0215646 A1 | 8/2009 | Anslyn et al. | |
| 2009/0256679 A1 | 10/2009 | Potyrailo et al. | |
| 2009/0265037 A1 | 10/2009 | Bassa | |
| 2009/0289776 A1 | 11/2009 | Moore et al. | |
| 2009/0308155 A1 | 12/2009 | Zhang | |
| 2010/0021993 A1 | 1/2010 | Wang et al. | |
| 2010/0042338 A1 | 2/2010 | Giurgiutiu et al. | |
| 2010/0059221 A1 | 3/2010 | Vannuffelen et al. | |
| 2010/0075405 A1 | 3/2010 | Broadley | |
| 2010/0102004 A1 | 4/2010 | Holland | |
| 2010/0138267 A1 | 6/2010 | Vittal et al. | |
| 2010/0153323 A1 | 6/2010 | Hennessy et al. | |
| 2010/0231407 A1 | 9/2010 | Carr | |
| 2010/0250170 A1 | 9/2010 | Kalinin et al. | |
| 2010/0261226 A1 | 10/2010 | Niazi | |
| 2010/0280788 A1 | 11/2010 | Bohan et al. | |
| 2010/0295558 A1 | 11/2010 | Eberheim et al. | |
| 2011/0006878 A1 | 1/2011 | Nyffeler et al. | |
| 2011/0006900 A1 | 1/2011 | Nyffeler et al. | |
| 2011/0012736 A1 | 1/2011 | Potyrailo et al. | |
| 2011/0018649 A1 | 1/2011 | David et al. | |
| 2011/0022318 A1 | 1/2011 | Zhao et al. | |
| 2011/0029156 A1 | 2/2011 | Vernacchia et al. | |
| 2011/0045601 A1 | 2/2011 | Gryska et al. | |
| 2011/0051775 A1 | 3/2011 | Ivanov et al. | |
| 2011/0117538 A1 | 5/2011 | Niazi | |
| 2011/0152706 A1 | 6/2011 | Christopherson et al. | |
| 2011/0152750 A1 | 6/2011 | Dacey, Jr. et al. | |
| 2011/0156177 A1 | 6/2011 | Merz | |
| 2011/0160681 A1 | 6/2011 | Dacey, Jr. et al. | |
| 2011/0221667 A1 | 9/2011 | Lee | |
| 2011/0248825 A1 | 10/2011 | Hamel et al. | |
| 2011/0263036 A1 | 10/2011 | Blauw et al. | |
| 2011/0282540 A1 | 11/2011 | Armitage et al. | |
| 2011/0283821 A1 | 11/2011 | Ober et al. | |
| 2012/0001730 A1 | 1/2012 | Potyrailo et al. | |
| 2012/0025526 A1 | 2/2012 | Luo et al. | |
| 2012/0053881 A1 | 3/2012 | Schulz et al. | |
| 2012/0231504 A1 | 9/2012 | Niazi | |
| 2012/0258441 A1 | 10/2012 | Gebauer et al. | |
| 2012/0265036 A1 | 10/2012 | Estes et al. | |
| 2012/0289757 A1 | 11/2012 | Boyden et al. | |
| 2013/0041334 A1 | 2/2013 | Prioleau et al. | |
| 2013/0060112 A1 | 3/2013 | Pryor et al. | |
| 2013/0182819 A1 | 7/2013 | Dvorkin et al. | |
| 2013/0285677 A1 | 10/2013 | Hammer | |
| 2014/0095102 A1 | 4/2014 | Potyrailo et al. | |
| 2014/0182362 A1 | 7/2014 | Potyrailo et al. | |
| 2014/0305194 A1 | 10/2014 | Surman et al. | |
| 2015/0185173 A1 | 7/2015 | Potyrailo et al. | |
| 2016/0187277 A1 | 6/2016 | Potyrailo et al. | |

FOREIGN PATENT DOCUMENTS

| | | |
|---|---|---|
| CN | 2809215 Y | 8/2006 |
| CN | 1865966 A | 11/2006 |
| CN | 101022760 A | 8/2007 |
| CN | 101057124 A | 10/2007 |
| CN | 201000455 Y | 1/2008 |

(56) References Cited

FOREIGN PATENT DOCUMENTS

| | | |
|---|---|---|
| CN | 102422330 A | 4/2012 |
| CN | 203923208 U | 11/2014 |
| EP | 2498076 A1 | 9/2012 |
| GB | 793953 A | 4/1958 |
| JP | 5774097 A | 5/1982 |
| JP | 59116855 U | 8/1984 |
| JP | 59160746 A | 9/1984 |
| JP | 0381659 A | 4/1991 |
| JP | 06160317 A | 6/1994 |
| JP | 06194333 A | 7/1994 |
| JP | 6086057 U | 12/1994 |
| JP | 0773282 A | 3/1995 |
| JP | 07120423 A | 5/1995 |
| JP | 08509549 A | 10/1996 |
| JP | 09292453 A | 11/1997 |
| JP | 10504388 A | 4/1998 |
| JP | 2000111547 A | 4/2000 |
| JP | 2001502791 A | 2/2001 |
| JP | 2002125206 A | 4/2002 |
| JP | 2003503011 A | 1/2003 |
| JP | 2003506706 A | 2/2003 |
| JP | 2003161637 A | 6/2003 |
| JP | 2005156569 A | 6/2005 |
| JP | 2006516721 A | 7/2006 |
| JP | 2007516509 A | 6/2007 |
| JP | 2008129009 A | 6/2008 |
| JP | 2008236617 A | 10/2008 |
| JP | 2008298565 A | 12/2008 |
| JP | 2009092633 A | 4/2009 |
| JP | 2009538433 A | 11/2009 |
| JP | 2009540292 A | 11/2009 |
| WO | 9845779 A1 | 10/1998 |
| WO | 00-55583 A1 | 9/2000 |
| WO | 0060120 A2 | 10/2000 |
| WO | 0173380 A1 | 10/2001 |
| WO | 0212129 A1 | 2/2002 |
| WO | 0223176 A1 | 3/2002 |
| WO | 03050529 A1 | 6/2003 |
| WO | 2004032191 A2 | 4/2004 |
| WO | 2007075619 A1 | 7/2007 |
| WO | 2007101992 A1 | 9/2007 |
| WO | 2008082654 A2 | 7/2008 |
| WO | 2013057630 A1 | 4/2013 |
| WO | 2015090358 A1 | 6/2015 |
| WO | 2015128050 A1 | 9/2015 |

OTHER PUBLICATIONS

Heeger, "Semiconducting and Metallic Polymers: The Fourth Generation of Polymeric Materials", The Journal of Physical Chemistry B, vol. No. 105, Issue No. 36, pp. 8475-8491, 2001.
Mourzina et al., "Development of Multisensor Systems based on Chalcogenide Thin Film Chemical Sensors for the Simulataneous Multicomponent Analysis of Metal Ions in Complex Solutions", Electrochimica Acta, vol. No. 47, Issue No. 1-2, pp. 251-258, Sep. 1, 2001.
Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.
Akyildiz et al., "Wireless Sensor Networks: A survey", Computer Networks, vol. No. 38, pp. 393-422, 2002.
Harpster et al., "A Passive Humidity Monitoring System for In-Situ Remote Wireless Testing of Micropackages", Microelectromechanical System, vol. No. 11, Issue No. 1, pp. 61-67, 2002.
Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, 2002.
Janata et al., "Electrochemical Sensors and their Impedances: A Tutorial", Critical Reviews in Analytical Chemistry, vol. No. 32, Issue No. 2, pp. 109-120, 2002.

Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, 2002.
Alary et al., "Subsea Water Separation: A Cost-effective Solution for Ultra Deep Water Production", 17th World Petroleum Congress, Rio de Janeiro, Brazil, Sep. 1-5, 2002.
Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.
Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.
Fauveau et al., "Guided-Wave RADAR helps Level-Detection in Harsh Settings Control Engineering", Control Engineering, vol. No. 50, Issue No. 3, pp. 16, Mar. 2003.
Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 2003.
Grimes et al., "Resonance Sensors: A Critical Review Sensors", Analytical Chemistry, vol. No. 75, Issue No. 8, pp. 1868-1879, Apr. 15, 2003.
De Borba et al., "Determination of Sodium at Low Ng/L Concentrations in Simulated Power Plant Waters by Ion Chromatography", Journal of Chromatography, vol. No. 995, Issue No. 1-2, pp. 143-152, May 2, 2003.
Sakharov et al., "Liquid Level Sensor using Ultrasonic Lamb Waves", Ultrasonics, vol. No. 41, Issue No. 4, pp. 319-322, Jun. 2003.
Kumar et al., "Investigation into the Interaction between Surface-Bound Alkylamines and Gold Nanoparticles", Langmuir, vol. No. 19, Issue No. 15, pp. 6277-6282, 2003.
Potyrailo et al., "Fluorescence Spectroscopy and Multivariate Spectral Descriptor Analysis for High-Throughput Multiparameter Optimization of Polymerization Conditions of Combinatorial 96-Microreactor Arrays", Journal of Combinatorial Chemistry, vol. No. 5, Issue No. 1, pp. 8-17, 2003.
Mabic et al., "Quality Adjustment of Treated Water in an Experimental Detection", GIT Labor-Fachzeitschrift, vol. No. 47, pp. 724-727, 2003.
Pasquale, "Mechanical Sensors and Actuators", Sensors and Actuators, A: Physical, vol. No. 106, Issue No. 1-3, pp. 142-148, 2003.
Chopra et al., "Selective Gas Detection Using a Carbon Nanotube Sensor", Applied Physics Letters, vol. No. 83, pp. 2280-2282, 2003.
Janata et al., "Conducting Polymers in Electronic Chemical Sensors", Nature Materials, vol. No. 2, pp. 19-24, 2003.
Bauer et al., "Resonant Nanocluster Technology—From Optical Coding and High Quality Security Features to Biochips", Nanotechnology, vol. No. 14, Issue No. 12, pp. 1289-1311, Nov. 4, 2003.
Joseph et al., "Chemiresistor Coatings from Pt- and Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15, 2004.
Shamsipur et al., "New Macrocyclic Diamides as Neutral Ionophores for Highly Selective and Sensitive PVC-Membrane Electrodes for Be2+ Ion", Electroanalysis, vol. No. 16, Issue No. 4, pp. 282-288, Mar. 2004.
Fransen, "New Control System Detects Desalter Problems before Upsets Occur", Agar Corporation, Prepared for presentation at the Aiche 2004 Spring National Meeting, Apr. 2004.
Bennett et al., "Monitoring the Operation of an Oil/Water Separator using Impedance Tomography", Minerals Engineering, vol. No. 17, Issue No. 5, pp. 605-614, May 2004.
Pavlov et al., "Aptamer-Functionalized Au Nanoparticles for the Amplified Optical Detection of Thrombin", Journal of the American Chemical Society, vol. No. 126, Issue No. 38, pp. 11768-11769, 2004.
Varma et al., "High-Speed Label-Free Detection by Spinning-Disk Micro-Interferometry", Biosensors and Bioelectronics, vol. No. 19, Issue No. 11, pp. 1371-1376, 2004.

(56) References Cited

OTHER PUBLICATIONS

Seyfried et al., "Measurement of Soil Water Content with a 50-MHz Soil Dielectric Sensor", Soil Science Society of America, vol. No. 68, Issue No. 2, pp. 394-403, 2004.
Want et al., "Enabling Ubiquitous Sensing with RFID", Computer, vol. No. 37, Issue No. 4, pp. 84-86, 2004.
Briglln et al., "Detection of Organic Mercaptan Vapors using Thin Films of Alkylamine-Passivated Gold Nanocrystals", Langmuir, vol. No. 20, Issue No. 2, pp. 299-305, 2004.
Kenishi et al., "The Dielectric Characteristics of Agricultural Land for On-site and Real Time Measurement", SICE 2004 Annual Conference on, IEEE Xplore, vol. No. 2, pp. 1489-1492, Aug. 4-6, 2004.
Thomas et al., "Conjugated Polymer Sensors: Design Principles Towards Enhanced Versatility", Report No. A035334, 2 pages, Dec. 2004.
Rose et al., "Sensitivity Gains in Chemosensing by Lasing Action in Organic Polymers", Nature, vol. No. 434, pp. 876-879, Apr. 14, 2005.
Holstad et al., "Scattered Gamma Radiation Utilized for Level Measurements in Gravitational Separators", IEEE Sensors, vol. No. 5, Issue No. 2, pp. 175-182, Apr. 2005.
Cheung et al., "Impedance Spectroscopy Flow Cytometry: on-Chip Label-Free cell Differentiation", Cytometry A, vol. No. 65, Issue No. 2, pp. 124-132, Jun. 2005.
Jang et al., "Chemical Sensors Based on Highly Conductive Poly(3,4-Ethylene-Dioxythiophene) Nanorods", Advanced Materials, vol. No. 17. Issue No. 13, pp. 1616-1620, Jul. 2005.
Rakow et al., "Molecular Recognition and Discrimination of Amines with a Colorimetric Array", Angewandte Chemie, vol. No. 44, Issue No. 29, pp. 4528-4532, Jul. 18, 2005.
Zhang et al., "Colorimetric Sensor Array for Organics in Water", Journal of the American Chemical Society, vol. No. 127, Issue No. 33, pp. 11548-11549, 2005.
Jaworski et al., "Measurements of Oil-Water Separation Dynamics in Primary Separation Systems Using Distributed Capacitance Sensors", Flow Measurement and Instrumentation, vol. No. 16, Issue No. 2-3, pp. 113-127, 2005.
Buhrdorf et al., "Multiparameteric Oil Condition Sensor Based on the Tuning Fork Technology for Automotive Applications", Book chapter in Advanced Microsystems for Automotive Applications, pp. 289-298, 2005.
Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, 2005.
Chuang et al., "Embeddable Wireless Strain Sensor Based on Resonant RF Cavities", Review of Scientific Instruments, vol. No. 20, pp. 1-7, Sep. 2005.
Bang et al., "A Novel Electrochemical Detection Method for Aptamer Biosensors", Biosensors and Bioelectronics, vol. No. 21, Issue No. 6, pp. 863-870, Dec. 15, 2005.
Locklin et al., "Effect of Morphology on Organic Thin Film Transistor Sensors", Analytical and Bioanalytical Chemistry, vol. No. 384, Issue No. 2, pp. 336-342, Jan. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 2006.
Casanella et al., "Oil-water Interface Level Sensor Based on an Electrode Array" , Instrumentation and Measurement Technology Coference, Sorrento, Italy, pp. 710-713, Apr. 24-27, 2006.
Lange et al., "Measuring Biomolecular Binding Events with a Compact Disc Player Device", Angewandte Chemie International Edition, vol. No. 45, pp. 270-273, 2006.
US Non-Final Rejection issued in connection with corresponding U.S. Appl. No. 12/325,653 on Nov. 16, 2012.
US Non-Final Rejection issued in connection with corresponding U.S. Appl. No. 12/977,599 on Feb. 5, 2013.
US Final Rejection issued in connection with corresponding U.S. Appl. No. 12/824,436 on Feb. 6, 2013.
US Non-Final Rejection issued in connection with corresponding U.S. Appl. No. 12/942,732 on Feb. 7, 2013.
De Souza et al., "A Close Dielectric Spectroscopic Analysis of Diesel/Biodiesel Blends and Potential Dielectric Approaches for Biodiesel Content Assessment", Fuel, vol. No. 105, pp. 705-710, Mar. 2013.
Swiech et al., "Dielectric Properties of Synthetic Oil Sands", Society of Petroleum Engineers—SPE Heavy Oil conference Canada, vol. no. 1, pp. 238-248, 2013.
Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.
US Final Rejection issued in connection with corresponding U.S. Appl. No. 12/325,653 on Aug. 8, 2013.
Unofficial English Translation of Japanese Office Action issued in connection with corresponding JP Application No. 2011-538590 on Oct. 8, 2013.
PCT Search Report and Written Opinion issued in connection with corresponding PCT Application No. PCT/SE2013/050671 on Nov. 18, 2013.
PCT Search Report and Written Opinion issued in connection with corresponding PCT Application No. PCT/US2013/058932 on Dec. 12, 2013.
PCT Search Report and Written Opinion issued in connection with corresponding PCT Application No. PCT/US2013/058898 on Dec. 18, 2013.
Unofficial English Translation of Chinese Office Action issued in connection with corresponding CN Application No. 2011800319590.6 on Dec. 26, 2013.
US Non-Final Rejection issued in connection with corresponding U.S. Appl. No. 12/977,568 on Jan. 16, 2014.
US Non-Final Rejection issued in connection with corresponding U.S. Appl. No. 12/827,623 on Jan. 30, 2014.
European Search Report and Opinion issued in connection with corresponding EP Application No. 11801238.4 on Mar. 5, 2014.
US Non-Final Rejection issued in connection with corresponding U.S. Appl. No. 12/325,653 on Mar. 17, 2014.
PCT Search Report and Written Opinion issued in connection with corresponding PCT Application No. PCT/SE2013/051590 on May 6, 2014.
PCT Search Report and Written Opinion issued in connection with corresponding PCT Application No. PCT/SE2013/051589 on May 6, 2014.
US Non-Final Rejection issued in connection with corresponding U.S. Appl. No. 13/630,939 on Aug. 11, 2014.
US Non-Final Rejection issued in connection with corresponding U.S. Appl. No. 14/031,965 on Aug. 26, 2014.
Soleimani et al., "Base Oil Oxidation Detection using Novel Chemical Sensors and Impedance Spectroscopy Measurements", Sensors and Actuators B: Chemical, vol. No. 199, pp. 247-258, Aug. 2014.
US Non-Final Rejection issued in connection with corresponding U.S. Appl. No. 14/031,951 on Sep. 2, 2014.
US Final Rejection issued in connection with corresponding U.S. Appl. No. 12/325,653 on Sep. 12, 2014.
Toledo et al., "Application of Quartz Tuning Forks and Extensional Microresonators for Viscosity and Density Measurements in Oil/Fuel Mixtures", Microsystem Technologies, vol. No. 20, Issue No. 4, pp. 945-953, 2014.
US Non-Final Rejection issued in connection with corresponding U.S. Appl. No. 13/484,674 on Nov. 3, 2014.
US Non-Final Rejection issued in connection with corresponding U.S. Appl. No. 13/558,499 on Dec. 4, 2014.
US Non-Final Rejection issued in connection with corresponding U.S. Appl. No. 13/630,954 on Dec. 15, 2014.
US Non-Final Rejection issued in connection with corresponding U.S. Appl. No. 13/729,800 on Dec. 19, 2014.
US Final Rejection issued in connection with corresponding U.S. Appl. No. 13/630,939 on Jan. 28, 2015.
US Non-Final Rejection issued in connection with corresponding U.S. Appl. No. 13/630,739 on Feb. 25, 2015.

(56) References Cited

OTHER PUBLICATIONS

Unofficial English Translation of Chinese Office Action issued in connection with corresponding CN Application No. 201180032850.4 on Mar. 2, 2015.
Unofficial English Translation of Japanese Office Action issued in connection with corresponding JP Application No. 2013518325 on Mar. 24, 2015.
Unofficial English Translation of Chinese Office Action issued in connection with corresponding CN Application No. 201110461799.0 on Mar. 30, 2015.
Zhu et al.,"An Integrated Lubricant Oil Conditioning Sensor Using Signal Multiplexing", Journal of Micromechanics and Micro engineering, vol. No. 25, Issue No. 1, pp. 1-12, 2015.
Unofficial English Translation of Japanese Office Action issued in connection with corresponding JP Application No. 2013-518328 on Apr. 7, 2015.
US Non-Final Rejection issued in connection with corresponding U.S. Appl. No. 13/729,851 on Apr. 28, 2015.
US Non-Final Rejection issued in connection with corresponding U.S. Appl. No. 13/630,587 on Jun. 2, 2015.
US Final Rejection issued in connection with corresponding U.S. Appl. No. 13/630,739 on Jun. 4, 2015.
US Non-Final Rejection issued in connection with corresponding U.S. Appl. No. 13/838,884 on Jun. 17, 2015.
PCT Search Report and Written Opinion issued in connection with corresponding PCT Application No. PCT/US2015/027482 on Jul. 15, 2015.
Unofficial English Translation of Japanese Notice of Allowance issued in connection with corresponding JP Application No. 2011-258627 on Aug. 4, 2015.
Taiwan Office Action issued in connection with corresponding TW Application No. 100146015 on Aug. 6, 2015.
US Non-Final Rejection issued in connection with corresponding U.S. Appl. No. 13/630,939 on Sep. 14, 2015.
Unofficial English Translation of Japanese Grant of Patent issued in connection with corresponding JP Application No. 2013518325 on Sep. 15, 2015.
US Non-Final Rejection issued in connection with corresponding U.S. Appl. No. 13/538,570 on Oct. 22, 2015.
European Search Report and Opinion issued in connection with corresponding EP Application No. 11801234.3 on Oct. 28, 2015.
Unofficial English Translation of Chinese Office Action issued in connection with corresponding CN Application No. 201380043615.6 on Nov. 9, 2015.
US Non-Final Rejection issued in connection with corresponding U.S. Appl. No. 12/824,436 on Dec. 2, 2015.
Misra, "Guide to Wireless Sensor Networks", Computer Communications and Networks, Jan. 1, 2009 (summary).
Ertl et al., "Interdigitated Impedance Sensors for Analysis of Biological Cells in Microfluidic Biochips", E & I Elektrotechnik and Informationstechnik, vol. No. 126, Issue No. 1, pp. 47-50, Feb. 2009.
Potyrailo et al., "Selective Detection of Chemical Species in Liquids and Gases using Passive Radio-Frequency Identification (RFID) Sensors", Proc. Transducers, pp. 1650-1653, 2009.
McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, 2009.
Sweden Office Action issued in connection with corresponding SE Application No. 0702495-3 on Jan. 26, 2009.
Potyrailo et al., "Development of Radio-Frequency Identification Sensors Based on Organic Electronic Sensing Materials for Selective Detection of Toxic Vapors", Journal of Applied Physics, vol. No. 106, Issue No. 12, pp. 124902-1 to 124902-6, 2009.
Jaworski et al., "On-line Measurement of Separation Dynamics in Primary Gas/Oil/Water Separators: Challenges and Technical Solutions—A review", Petroleum Science and Engineering, vol. No. 68, pp. 47-59, 2009.

Potyrailo et al., "Combinatorial Screening of Polymeric Sensing Materials Using RFID Sensors",Journal of Combinatorial Chemistry, vol. No. 11, Issue No. 4, pp. 598-603, 2009.
Westafer et al., "Functionalization of High Frequency SAW RFID Devices for Ozone Dosimetry", IEEE Sensors, pp. 1747-1752, Oct. 25-28, 2009.
Sweden Office Action issued in connection with corresponding SE Application No. 0702495-3 on Sep. 29, 2009.
PCT Search Report and Written Opinion issued in connection with corresponding PCT Application No. PCT/SE2009/051346 on Mar. 15, 2010.
US Non-Final Rejection issued in connection with corresponding U.S. Appl. No. 11/560,476 on Apr. 5, 2010.
Potyrailo et al. "Integration of Passive Multivariable RFID Sensors into Single-Use Biopharmaceutical Manufacturing Components", RFID, 2010 IEEE International, pp. 1-7, Apr. 2010.
Potyrailo et al., "Selective Quantitation of Vapors and their Mixtures using Individual Passive Multivariable RFID Sensors", RFID, 2010 IEEE International, pp. 22-28, Apr. 2010.
Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.
Hong et al., "Development of a Micro Liquid-Level Sensor for Harsh Environments using a Periodic Heating Technique", Measurement Science and Technology, vol. No. 21, Issue No. 10, 2010.
Potyrailo et al., "A Passive Radio Frequency Identification (RFID) Chemical Sensors for Homeland Security Applications", In Wiley Handbook of Science and Technology for Homeland Security, vol. No. 1, pp. 523-544, 2010.
Wang et al., "Flexible Chemiresistor Sensors: Thin Film Assemblies of Nanoparticles on a Polyethylene Terephthalate Substrate", Journal of Materials Chemistry, vol. No. 20, pp. 907-915, 2010.
Alexander et al., "Optimization of Interdigitated Electrode (IDE) Arrays for Impedance Based Evaluation of Hs 578T Cancer Cells", Journal of Physics: Conference Series, vol. No. 24, Issue No. 1, pp. 1-4, 2010.
Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.
Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, 2010.
Cho et al., "Capacitive Sensor for Automotive Engine Oil Degradation using Wireless Network", International Symposium on Advanced Packaging Materials: Microtech, APM '10 , pp. 88-91, 2010.
De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, 2010.
Bianchi et al., "Model of an Interdigitated Microsensor to Detect and Quantify Cells Flowing in a Test Chamber", 6th annual COMSOL Conference Paris, pp. 1-5, Nov. 2010.
Suresh et al., "Piezoelectric Based Resonant Mass Sensor using Phase Measurement", Measurement, vol. No. 44, Issue No. 2, pp. 320-325, Feb. 2011.
Perez et al., "Low-Cost Oil Quality Sensor Based on Changes in Complex Permittivity", Sensors, vol. No. 11, pp. 10675-10690, 2011.
Potyrailo et al. "RFID Sensors as the Common Sensing Platform for Single-Use Biopharmaceutical Manufacturing", Measurement Science and Technology, vol. No. 22, 2011.
Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2011.
Owenier et al., "Dielectric Permittivity of Geologic Materials at Different Water Contents—Measurements with an Impedance Ana-

(56) References Cited

OTHER PUBLICATIONS lyzer", 6th International Workshop on Advanced Ground Penetrating Radar (IWAGPR), pp. 1-5, Jun. 22-24, 2011.
Potyrailo et al., "Multivariable Passive RFID Vapor Sensors: Pilot-Scale Manufacturing and Laboratory Evaluation", IEEE International Conference on RFID, Poster 52, 2011.
US Non-Final Rejection issued in connection with corresponding U.S. Appl. No. 12/424,016 on Jul. 12, 2011.
Guan et al.,"Application of Dielectric Spectroscopy for Engine Lubricating Oil Degradation Monitoring", Sensors and Actuators A: Physical, vol. No. 168, Issue No. 1, pp. 22-29, Jul. 2011.
Wang et al., "Impedance Analysis for Lateral Field Excited Acoustic Wave Sensors", Sensors and Actuators B: Chemical, vol. No. 156, Issue No. 2, pp. 969-975, Aug. 2011.
Sen et al., "Evaluation of Sensor Arrays for Engine Oils Using Artificial Oil Alteration", Proceedings of SPIE 8066, Smart Sensors Actuators and MEMS V, 2011.
Latif et al., "Conductometric Sensors for Monitoring Degradation of Automotive Engine Oil", Sensors, vol. No. 11, Issue No. 9, pp. 8611-8625, Sep. 2011.
PCT Search Report and Written Opinion issued in connection with corresponding PCT Application No. PCT/SE2011/050748 on Oct. 5, 2011.
PCT Search Report and Written Opinion issued in connection with corresponding PCT Application No. PCT/SE2011/050818 on Oct. 24, 2011.
Potyrailo et al., "Materials and Transducers Toward Selective Wireless Gas Sensing", Chemical Reviews, vol. No. 111, Issue No. 11, pp. 7315-7354, Nov. 9, 2011.
Datla et al., "Wireless Distributed Computing: A Survey of Research Challenges", IEEE Communications Magazine, vol. No. 50, Issue No. 1, pp. 144-152, Jan. 2012.
Combined GB Search and Examination Report issued in connection with corresponding GB Application No. GB1121548.0 on Mar. 28, 2012.
Vasilyeva et al., "Differences in Behaviour of Adsorbed Water in Kaolinites and Montmorillonites in Temperature Range from −90° C. to +140° C. by Dielectric Spectroscopy", Physics: Conference Series, vol. No. 394, Issue No. 1, pp. 1-6, 2012.
Aghayan, "On-Line Monitoring of Engine Health through the Analysis of Contaminants in Engine Lubricant", The School of Graduate and Postdoctoral Studies the University of Western Ontario London, Ontario, Canada, pp. 1-273, 2012.
US Non-Final Rejection issued in connection with corresponding U.S. Appl. No. 12/824,436 on Aug. 8, 2012.
Fochtmann et al., "Optimization of the Lateral Field Excited Platform for Liquid Sensing Applications", Sensors and Actuators B: Chemical, vol. No. 170, pp. 95-103, Jul. 1, 2012.
US Non-Final Rejection issued in connection with corresponding U.S. Appl. No. 11/560,476 on Jul. 5, 2012.
Datla et al., "Wireless Distributed Computing in Cognitive Radio Networks", Ad Hoc Networks, vol. No. 10, Issue No. 05, pp. 845-857, Jul. 2012.
Unofficial English Translation of Japanese Office Action issued in connection with corresponding JP Application No. 2007291481 on Aug. 7, 2012.
US Non-Final Rejection issued in connection with corresponding U.S. Appl. No. 13/331,003 on Sep. 10, 2012.
US Notice of Allowance issued in connection with corresponding U.S. Appl. No. 12/424,016 on Sep. 28, 2012.
Chinese Office Action issued in connection with corresponding CN Application No. 200980149087.6 on Sep. 13, 2012.
Yang, "Sensors and Instrumentation for Monitoring and Control of Multi-Phase Separation", Measurement and control, vol. No. 39, Issue No. 6, pp. 178-184, Jul. 2006.
Morris et al., "Wireless Sensor Array System for Combinatorial Screening of Sensor Materials", Combinatorial Methods and Informatics in Materials Science, vol. No. 894, pp. 219-224, 2006.

Yang et al., "Chemical Identification Using an Impedance Sensor Based on Dispersive Charge Transport", Applied Physics Letters, vol. No. 88, pp. 1-3, 2006.
Pejcic et al., "Impedance Spectroscopy: Over 35 Years of Electrochemical Sensor Optimization", Electrochimica Acta, vol. No. 51, Issue No. 28, pp. 6217-6229, Sep. 15, 2006.
Benini et al., "Wireless Sensor Networks: Enabling Technology for Ambient Intelligence", Microelectronics Journal, vol. No. 37, Issue No. 12, pp. 1639-1649, Dec. 2006.
Bai et al., "Gas Sensors Based on Conducting Polymers", Sensors (Basel), vol. No. 7, Issue No. 3, pp. 267-307, Mar. 2007.
Casanella et al., "Continuous Liquid Level Measurement Using a Linear Electrode Array", Measurement Science and Technology, vol. No. 18, Issue No. 7, pp. 178-184, May 9, 2007.
Liu et al., "Measurement of Density and Viscosity of Dodecane and Decane with a Piezoelectric Tuning Fork Over 298-448 K and 0.1-137.9 MPa", Sensors and Actuators A Physical, vol. No. 167, Issue No. 2, pp. 347-353, Jun. 2007.
Lu et al., "MEMS-Based Inductively Coupled RFID Transponder for Implantable Wireless Sensor Applications", IEEE Transactions on Magnetics, vol. No. 43, Issue No. 6, pp. 2412-2414, 2007.
Potyrailo et al., "Multianalyte Chemical Identification and Quantitation Using a Single Radio Frequency Identification Sensor", Analytical Chemistry, vol. No. 79, Issue No. 1, pp. 45-51, 2007.
Potyrailo et al., "Wireless Resonant Sensor Array for High-Throughput Screening of Materials", Review of Scientific Instruments, vol. No. 78, 2007.
Sugiyasu et al., "Conducting-Polymer-Based Chemical Sensors: Transduction Mechanisms", Bulletin of the Chemical Society of Japan, vol. No. 80, pp. 2074-2083, 2007.
Tan et al., "A Wireless, Passive Sensor for Quantifying Packaged Food Quality", Sensors, vol. No. 7, Issue No. 9, pp. 1747-1756, 2007.
Gutzeit, "Controlling Crude Unit Overhead Corrosion—Rules of Thumb for Better Crude Desalting", NACE International Corrosion Conference Series, pp. 075671-0756721, 2007.
Hua et al., "Gas sensor based conducting polymers", Sensors, vol. No. 7, pp. 267-307, 2007.
Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, 2007.
Armani et al., "Single-Molecule Detection with Optical Microcavities", Science, vol. No. 317, Issue No. 5839, pp. 783-787, Aug. 10, 2007.
Hempel et al., "5D-2 Application of a Portable RF Impedance Spectrum Analyzer for the Investigation of Lateral Field Excited Acoustic Wave Sensors in a Liquid Environment", Ultrasonics Symposium, pp. 373-376, 2007.
Li et al., "Chemosensory Performance of Molecularly Imprinted Fluorescent Conjugated Polymer Materials", Journal of the American Chemical Society, vol. No. 129, Issue No. 51, pp. 15911-15918, 2007.
Li et al., "Inkjet Printed Chemical Sensor Array Based on Polythiophene Conductive Polymers", Sensors and Actuators B, vol. No. 123, pp. 651-660, 2007.
Wang et al., "A New Method for On-line Monitoring of Brake Fluid Condition using an Enclosed Reference Probe", Measurement Science and Technology, vol. No. 18, Issue No. 11, pp. 3625-3635, 2007.
Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.
Wei et al., "Simple and Sensitive Aptamer-Based Colorimetric Sensing of Protein using Unmodified Gold Nanoparticle Probes", Chemical Communications, pp. 3735-3737, 2007.
Metzger et al., "Low-cost Weight-sensitive Foam to Monitor Product Availability on Retail Shelves", International conference on Pervasive Computing (Pervasive2007), pp. 268-279, 2007.
Hewitt, "Oil/Water Interface Control for Desalters", Petroleum Technology Quarterly 2007, vol. No. 12, Issue No. 5, pp. 75-78, 2007.

(56) References Cited

OTHER PUBLICATIONS

Hwili et al., "Multi-Modality Multi-Interface Level Measurement", Physics: Conference Series, vol. No. 76, Issue No. 1, pp. 1-6, 2007.

Wang et al., "A Gold Nanoparticle-Based Aptamer Target Binding Readout for ATP Assay", Advanced Materials, vol. No. 19, Issue No. 22, pp. 3943-3946, Nov. 2007.

Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.

Wang et al., "Aptamer Biosensor for Protein Detection using Gold Nanoparticles", Analytical Biochemistry, vol. No. 373, Issue No. 2, pp. 213-219, Feb. 15, 2008.

Wang et al., "Electrochemical Sensors for Clinic Analysis", Sensors (Basel), vol. No. 8, Issue No. 4, pp. 2043-2081, Apr. 2008.

Potyrailo et al., "Position-Independent Chemical Quantitation with Passive 13.56-Mhz Radio Frequency Identification (RFID) Sensors", Talanta, vol. No. 75, Issue No. 3, pp. 624-628, May 15, 2008.

Röck et al., "Electronic Nose: Current Status and Future Trends", Chemical Reviews, vol. No. 108, pp. 705-725, 2008.

Jimenez et al., "Surface Characterization of Clay Particles via Dielectric Spectroscopy", Annales Umcs, Chemistry, vol. No. 63, Issue No. 1, pp. 73-86, Jan. 2008.

Xiang-Hong et al., "Sensors and Biosensors for the Determination of Small Molecule Biological Toxins", Sensors, vol. No. 8, Issue No. 9, pp. 6045-6054, 2008.

Metzger et al., "Flexible-Foam-Based Capacitive Sensor Arrays for Object Detection at Low Cost", Applied Physics Letters, vol. No. 92, Issue No. 1, 2008.

Zheng et al., "Resonance Impedance Sensing of Human Blood Cells", Sensors and Actuators A: Physical, vol. No. 145-146, pp. 29-36, 2008.

Potyrailo et al., "Modeling of Selectivity of Multi-Analyte Response of Passive Radio Frequency Identification (RFID) Sensors", 12th International Meeting on Chemical Sensors, Columbus, 2008.

Hempel et al., "Lateral Field Excited Quartz Crystal Resonator Sensors for Determination of Acoustic and Electrical Properties of Liquids", IEEE International Frequency Control Symposium, pp. 705-710, 2008.

Potyrailo et al., "RFID Sensors based on Ubiquitous Passive 13.56-MHz RFID Tags and Complex Impedance Detection", Wireless Communications and Mobile Computing, pp. 1-13, 2008.

UID, "Ultrasonic Interface Level Detector", Christian Michelsen Research, 2008.

Capone et al., "Metal Oxide Gas Sensor Array for the Detection of Diesel Fuel in Engine Oil", Sensors and Actuators B: Chemical, vol. No. 131, pp. 125-133, 2008.

Diamond et al., "Wireless Sensor Networks and Chemo-/Biosensing", Chemical Reviews, vol. No. 108, Issue No. 2, pp. 652-679, 2008.

Hatchett et al., "Composites of Intrinsically Conducting Polymers as Sensing Nanomaterials", Chemical Reviews, vol. No. 108, Issue No. 2, pp. 746-769, 2008.

Joo et al., "Chemical Sensors with Integrated Electronics", Chemical Reviews, vol. No. 108, Issue No. 2, pp. 638-651, 2008.

Kauffman et al., "Carbon Nanotube Gas and Vapor Sensors", Angewandte Chemie International Edition, vol. No. 47, pp. 6550-6570, 2008.

Li et al., "Chemical Sensing Using Nanostructured Polythiophene Transistors", Nano Letters, vol. No. 8, Issue No. 11, pp. 3563-3567, 2008.

Palacios et al., "Rational Design of a Minimal Size Sensor Array for Metal Ion Detection", Journal of the American Chemical Society, vol. No. 130, Issue No. 31, pp. 10307-10314, 2008.

Hwili et al., "A Single Rod Multi-Modality Multi-Interface Level Sensor using an AC Current Source", IEEE International Workshop on Imaging Systems and Techniques, Sep. 10-12, 2008.

Guan et al., "Engine Lubricating Oil Classification by SAE Grade and Source Based on Dielectric Spectroscopy Data", Analytica Chimica Acta, vol. No. 628, Issue No. 1, pp. 117-120, Oct. 17, 2008.

Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.

Persaud et al., "Analysis of Discrimination Mechanisms in the Mammalian Olfactory System Using a Model Nose", Nature, vol. No. 299, pp. 352-355, Sep. 23, 1982.

Sen et al., "Frequency Dependent Dielectric and Conuctivity Response of Sedimentary Rocks", Journal of Microwave Power, vol. No. 18, Issue No. 1, pp. 95-105, 1983.

Raythatha et al., "Dielectric Properties of Clay Suspensions in MHz to GHz Range", Journal of Colloid and Interface Science, vol. No. 109, Issue No. 2, pp. 301-309, Feb. 1986.

Ward et al., "In Situ Interfacial Mass Detection with Piezoelectric Transducers", Science, vol. No. 249, Issue No. 1972, pp. 1000-1007, Aug. 31, 1990.

Shi et al., "Capacitance-Based Instrumentation for Multi-Interface Level Measurement", Measurement Science and Technology, vol. No. 2, Issue No. 10, pp. 923-933, 1991.

Wise et al., "Microfabrication Techniques for Integrated Sensors and Microsystem", Science, vol. No. 254, pp. 1335-1342, 1991.

Mullen et al., "Trace Detection of Ionic Species with Surface Enhanced Raman Spectroscopy", Spectroscopy, vol. No. 7, pp. 24-32, 1992.

Ervin et al., "Development of a Fiber-Optic Sensor for Trace Metal Detection in Aqueous Environments", Applied Optics, vol. No. 32, Issue No. 22, pp. 4287-4290, Aug. 1, 1993.

Agar et al., "Energy Absorption Probes Control Oily-Water Discharges", Hydrocarbon Processing, vol. No. 72, Issue No. 8, Aug. 1, 1993.

Wensink, "Dielectric Properties of Wet Soils in the Frequency Range 1-3000 MHz", Geophysical Prospecting, vol. No. 41, Issue No. 6, pp. 671-696, Aug. 1993.

Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.

Pal, "Techniques for Measuring the Composition (Oil and Water Content) of Emulsions-Astate of the Art Review", Colloids and Surfaces: A Physicochemical and Engineering Aspects, vol. No. 84, Issue No. 2-3, pp. 141-193, 1994.

Isaksen et al., "A Capacitance-Based Tomography System for Interface Measurement in Separation Vessels", Measurement Science and Technology, vol. No. 5, Issue No. 10, pp. 1262-1271, Jun. 1994.

Yang et al., "A Multi-Interface Level Measurement System using a Segmented Capacitance Sensor for Oil Separators", Measurement Science and Technology, pp. 1177-1180, Jul. 19, 1994.

Amrani et al., "High-Frequency Measurements of Conducting Polymers: Development of a New Technique for Sensing Volatile Chemicals", http://iopscience.iop.org/0957-0233/6/10/010; 8 Pages, 1995.

Legin et al "Development and Analytical Evaluation of a Multisensor System for Water Quality Monitoring", Sensors and Actuators B: Chemical, vol. No. 27, Issue No. 1-3, pp. 377-379, Jun. 1995.

Nicolaou et al., "Radiofrequency Encoded Combinatorial Chemistry", Angewandte Chemie International Edition, vol. No. 34, pp. 2289-2291, 1995.

Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, 1995.

Hutzler et al., "Measurement of Foam Density Profiles Using AC Capacitance", Europhysics Letters, vol. No. 31, Issue No. 8, pp. 497-502, Sep. 10, 1995.

Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.

(56) References Cited

OTHER PUBLICATIONS

Malinowska et al., "Enhanced Electrochemical Performance of Solid-State Ion Sensors Based on Silicone Rubber Membranes", Sensors and Actuators B: Chemical, vol. No. 43, Issue No. 1-3, pp. 161-167, Jul. 1996.
Amrani et al., "Multi-frequency Measurements of Organic Conducting Polymers for Sensing of Gases and Vapours", Sensors and Actuators B: Chemical, vol. No. 33, Issue No. 1-3, pp. 137-141, Jul. 1996.
Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.
Chinowski et al., "Experimental Data from a Trace Metal Sensor Combining Surface Plasmon Resonance with Anodic Stripping Voltametry", Sensors and Actuators B: Chemical, vol. No. 35, Issue No. 1-3, pp. 37-43, Sep. 1996.
Josse et al., "AC-Impedance-Based Chemical Sensors for Organic Solvent Vapors", Sensors and Actuators B: chemical, vol. No. 36, Issue No. 1-3, pp. 363-369, Oct. 1996.
Kress-Rogers, "Handbook of Biosensors and Electronic Noses: Medicine, Food, and the Environment", CRC Press, 20 pages, Oct. 24, 1996 (summary).
Santamarina et al., "Dielectric Permittivity of Soils Mixed With Organic and Inorganic Fluids (0.02ghz to 1.30 GHz)", Journal of Environmental and Engineering Geophysics, vol. No. 2, Issue No. 1, pp. 37-52, 1997.
Hammond et al., "An Acoustic Automotive Engine Oil Quality Sensor", Solid State Sensors and Actuators, vol. 2, pp. 1343-1346, Jun. 1997.
Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.
Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.
Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.
Wohltjen et al., "Colloidal Metal-Insulator-Metal Ensemble Chemiresistor", Anal.Chem, vol. No. 70, Issue No. 14, pp. 2856-2859, 1998.
Chyan et al., "Ultrapure Water Quality Monitoring by a Silicon-Based Potentiometric Sensor" Analyst, vol. No. 125, Issue No. 1, pp. 175-178, 1999.
Homola et al., "Surface Plasmon Resonance Sensors: Review", Sensors and Actuators B: Chemical, vol. No. 54, Issue No. 1-2, pp. 3-15, Jan. 25, 1999.
Jaworski et al., "A Capacitance Probe for Interface Detection in Oil and Gas Extraction Plant", Measurement of Science and Technology, vol. No. 10, Issue No. 3, pp. L15-L20, Jan. 1999.
Amrani et al., "Multi-Frequency Interrogation Technique Applied to Conducting Polymer Gas and Odour Sensors", vol. 146, pp. 95-101, Mar. 1999.
Schuller et al., "Advanced Profile Gauge for Multiphase Systems, 1st World Congress on Industrial Process Tomography", Buxton, Greater Manchester, Apr. 14-17, 1999.
Asskildit et al., "New Measuring Sensor for Level Detection in Subsea Separators", ABB Review, pp. 11-17, Apr. 1999.
Ishida et al., "Effects of pH on Dielectric Relaxation of Montmorillonite, Allophane, and Imogolite Suspensions, Colloid and Interface Science", ScienceDirect, vol. No. 212, Issue No. 1, pp. 152-161, Apr. 1999.
Legin et al., "The Features of the Electronic Tongue in Comparison with the Characterstics of the Discrete Ion Selective Sensor", Sensors and Actuators B: Chemical, vol. No. 58, Issue No. 1-3, pp. 464-468, Sep. 21, 1999.

Artmann, "Electronic Identification Systems: State of the Art and their Further Development", Computers and Electronics in Agriculture, vol. No. 24, Issue No. 1-2, pp. 5-26, Nov. 1999.
Jurs et al., "Computational Methods for the Analysis of Chemical Sensor Array Data from Volatile Analytes", Chemical Reviews, vol. No. 100, Issue No. 7, pp. 2649-2678, 2000.
McQuade et al., "Conjugated Polymer-Based Chemical Sensors", Chem. Rev, vol. No. 100, Issue No. 7, pp. 2537-2574, 2000.
Vlasov et al., "Electronic Tongue—New Analytical Tool for Liquid Analysis on the basis of Non-Specific Sensors and Methods of Pattern Recognition", Sensors and Actuators B: Chemical, vol. No. 65, Issue No. 1-3, pp. 235-236, Jun. 30, 2000.
Rakow et al., "A Colorimetric Sensor Array for Odour Visualization", Nature, vol. No. 406, pp. 710-713, Aug. 17, 2000.
Taton et al., "Scanometric DNA Array Detection with Nanoparticle Probes", Science, vol. No. 289, Issue No. 5485, pp. 1757-1760, Sep. 8, 2000.
Shirakawa, "The Discovery of Polyacetylene Film: The Dawning of an Era of Conducting Polymers", Angewandte Chemie International Edition, vol. No. 40, Issue No. 14, pp. 2574-2580, Jul. 16, 2001.
Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.
Kaya, "A Electrical Spectroscopy of Kaolin and Bentonite Slurries", Turkish Journal of Engineering and Environmental Sciences, vol. No. 25, pp. 345-354, 2001.
Lee, "Increase Oil Production and Reduce Chemical Usage through Separator Level Measurement by Density Profiling", ISA TECH/EXPO Technology Update Conference Proceedings, vol. No. 416, pp. 321-328, 2001.
International Search Report and Written Opinion dated Jan. 27, 2014 which was issued in connection with PCT Patent Application No. PCT/US13/55983 which was filed on Aug. 21, 2013.
Bauerle "Study of Solid Electrolyte Polarization by a Complex Admittance Method", Journal of Physics and Chemistry of Solids, vol. No. 30, Issue No. 12, pp. 2657-2670, Dec. 1969.
Matsui, "Complex-Impedance Analysis for the Development of Zirconia Oxygen Sensors", Solid State Ionics, vol. No. 3-4, pp. 525-529, Aug. 1981.
Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.
Ghiotti et al., "Moisture Effects on Pure and Pd-Doped SnO2 Thick Films Analysed by FTIR Spectroscopy and Conductance Measurements", Sensors and Actuators B: Chemical, vol. No. 25, Issue No. 1-3, pp. 520-524, Apr. 1995.
Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.
Amrani et al., "An Intelligent Gas Sensing System", Sensors and Actuators B: Chemical, vol. No. 44, Issue No. 1-3, pp. 512-516, Oct. 1997.
Basu et al., "Smart Sensing" of Oil Degradation and Oil Level Measurements in Gasoline Engines, SAE 2000 World congress, Detroit, Michigan, 2000-01-1366, pp. 1-7, Mar. 6-9, 2000.
Foster et al., "Detection of Trace Levels of Water in Oil by Photoacoustic Spectroscopy", Sensors and Actuators B: Chemical, vol. No. 77, Issue No. 3, pp. 620-624, Jul. 10, 2001.
Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.
Grimes et al., "Wireless Magnetoelastic Resonance Sensors: A Critical Review", vol. No. 2, Issue No. 7, pp. 294-313, Jul. 23, 2002.
Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.
Finkenzeller, "RFID Handbook: Fundamentals and Applications in Contactless Smart Cards and Identification", John Wiley & Sons, Ltd, Second Edition, pp. 1-427, Jul. 21, 2003.

(56) References Cited

OTHER PUBLICATIONS

Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.
Barsoukov et al., "Impedance Spectroscopy: Theory, Experiment, and Applications", Second Edition, pp. 205-264, 2005.
Lvovich et al., "Impedance Characterization of Industrial Lubricants", Electrochimica Acta, vol. No. 51, Issue No. 8-9, pp. 1487-1496, Jan. 20, 2006.
Qing et al., "RFID Tag Antennas", Antennas for Portable Devices, John Wiley & Sons, Ltd, pp. 59-61; 65-69, Mar. 2007.
Hendrick., "Cellulose Acetate Fibers with Fluorescing Nanoparticles for Anti-Counterfeiting Purposes", Erin Sue Hendrick, pp. 1-36, 2008.
Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.
Surman et al., "Quantitation of Toxic Vapors in Variable Humidity Atmosphere Using Individual Passive Radio Frequency Identification (RFID) Sensors", 12th International Meeting on Chemical Sensors, Columbus, pp. 1-2, 2008.
Agoston et al., "A Concept of an Infrared Sensor System for Oil Condition Monitoring", Elektrotechnik & Informationstechnik, vol. No. 125, Issue No. 3, pp. 71-75, Mar. 2008.
Wudy et al., "Rapid Impedance Scanning QCM for Electrochemical Applications Based on Miniaturized Hardware and High-Performance Curve Fitting", Electrochimica Acta, vol. No. 53, Issue No. 22, pp. 6568-6574, Sep. 20, 2008.
Sacristan-Riquelme et al., "Low Power Impedance Measurement Integrated Circuit for Sensor Applications", Microelectronics Journal, vol. No. 40, Issue No. 1, pp. 177-184, Jan. 2009.
Niedermayer et al., "Yet Another Precision Impedance Analyzer (YAPIA)—Readout Electronics for Resonating Sensors", Sensors and Actuators A: Physical, vol. No. 156, Issue No. 1, pp. 245-250, Nov. 2009.
Mortier et al., "Chemistry and Technology of Lubricants", Third Edition, Springer, pp. 1-560, 2010.
Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.
Agilent Impedance Measurement Handbook, "A Guide to Measurement Technology and Techniques", 4th Edition, Agilent Technologies, pp. 1-140, Sep. 10, 2013.
Elzagzoug et al., "Condition Monitoring of High Voltage Transformer Oils Using Optical Chromaticity", Measurement Science and Technology, vol. No. 25, Issue No. 6, pp. 1-9, Jun. 2014.
US Non-Final Rejection issued in connection with related U.S. Appl. No. 13/331,003 on Sep. 10, 2014.
Hoja et al., "Miniaturized Impedance Analyzer Using AD5933", Lecture Notes on Impedance Spectroscopy, vol. No. 5, pp. 93-100, Feb. 17, 2015.
Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.

Simic, "Complex Impedance Measurement System for the Frequency Range from 5 kHz to 100 kHz", Key Engineering Materials, vol. No. 644, pp. 133-136, May 11, 2015.
Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.
Ghaffari et al., "A Wireless Multi-Sensor Dielectric Impedance Spectroscopy Platform", Sensors, vol. No. 15, Issue No. 9, pp. 23572-23588, Sep. 17, 2015.
Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.
Poseidon Systems, "Oil Quality Products", TRIDENT QM1100; TRIDENT QM2100; TRIDENT WM800, pp. 1-3, Retrieved from http://www.poseidonsys.com/products/oil-quality on Dec. 24, 2015.
Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.
Chinese Office Action issued in connection with related CN Application No. 201380050788.0 on Jan. 20, 2016.
PCT Search Report and Written Opinion issued in connection with related PCT Application No. PCT/EP2015/075026 on Feb. 1, 2016.
AU Examination Report issued in connection with corresponding AU Application No. 2013305814 on Jun. 10, 2016.
Ex Parte Quayle Action issued in connection with related U.S. Appl. No. 14/532,168 on Aug. 4, 2016.
Eurasian Search Report issued in connection with related EA Application No. 201592216 on Aug. 4, 2016.
Unofficial English Translation of Chinese Office Action issued in connection with related CN Application No. 212800701655.5 on Jul. 13, 2016.
US Non-Final Office Action issued in connection with related U.S. Appl. No. 12/824,436 on Sep. 6, 2016.
European Search Report and Opinion issued in connection with related EP Application No. 09830658.2 on Sep. 16, 2016.
Australian Examination Report issued in connection with related AU Application No. 2015268746 on Oct. 21, 2016.
US Supplemental Notice of Allowability issued in connection with related U.S. Appl. No. 14/532,168 on Oct. 25, 2016.
US Non-Final Rejection issued in connection with related U.S. Appl. No. 14/697,086 on Oct. 31, 2016.
Unofficial English Translation of Japanese Search Report issued in connection with related JP Application No. 2011258627 on Dec. 1, 2016.
U.S. Appl. No. 14/869,038, filed Sep. 29, 2015, Bret Dwayne Worden et al.
U.S. Appl. No. 14/866,320, filed Sep. 25, 2015, Radislav Alexandrovich Potyrailo et al.
U.S. Appl. No. 14/585,690, filed Dec. 30, 2014, Radislav Alexandrovich Potyrailo et al.
U.S. Appl. No. 61/987,853, filed May 2, 2014, Cheryl Margaret Surman et al.
U.S. Appl. No. 62/271,030, filed Dec. 22, 2015, Cheryl Margaret Surman et al.
U.S. Appl. No. 13/538,570, filed Jun. 29, 2012, Radislav Alexandrovich Potyrailo et al.

* cited by examiner

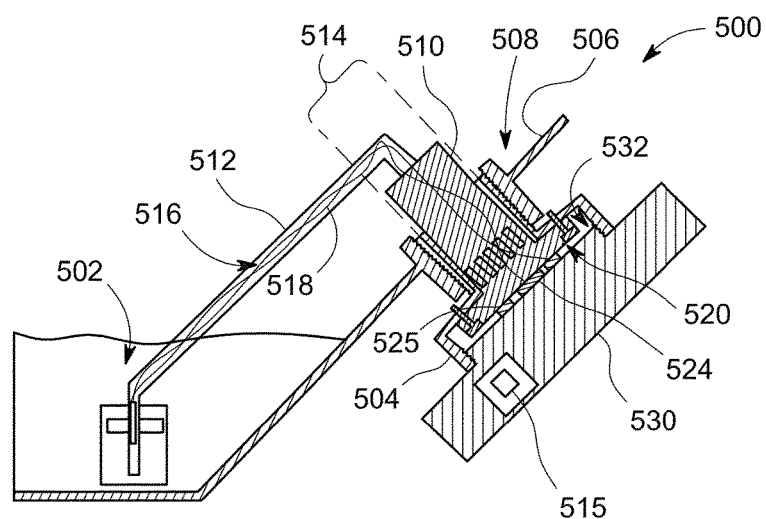
FIG. 11
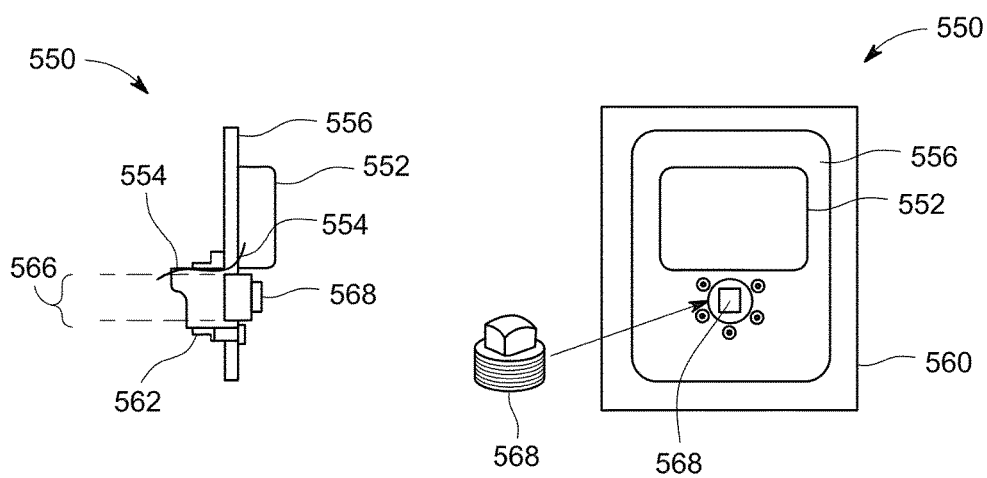
FIG. 12
FIG. 13

WIRELESS SYSTEM AND METHOD FOR MEASURING AN OPERATIVE CONDITION OF A MACHINE

CROSS-REFERENCE TO RELATED APPLICATIONS

The present application claims the benefit of U.S. Provisional Patent Application No. 61/692,230, filed on Aug. 22, 2012, which is incorporated herein by reference in its entirety.

FIELD

One or more embodiments of the subject matter described herein generally relate to systems and methods for detecting an operative condition of a machine or a component of the machine that has movable parts.

BACKGROUND

Many industrial machines (e.g., locomotives, trucks, earth-moving equipment, windmills, and the like) include elements or assemblies (e.g., mechanical drive trains) that operate within difficult environments and/or endure substantial amounts of thermal or torsional stress as well as shock and vibration. It is often desirable to monitor a condition of an element or assembly so that it may be replaced or repaired before severe and permanent damage is sustained by the machine. Often, fluid lubricants are used to provide lubrication and cooling to increase performance of the machine and/or to increase the lifetime operation of the machine. Lubricants reduce the friction between two parts that engage each other and may also dissipate heat that is generated by the friction between the two parts. As one specific example, speed control from a traction motor or other provider of mechanical power may be accomplished with a gear train or drive train. Gear trains typically include at least two gears that engage each other. For instance, teeth of a first gear (e.g., pinion gear) may engage teeth of a larger gear at a gear mesh. It is common for the gears to be lubricated by a lubricant (e.g., oil) to reduce the friction between the gears and to facilitate the dissipation of heat that is generated during operation. In order for the gears to be suitably lubricated, a designated amount of lubricant is available for use by the gears.

A gear train may include a gear case that surrounds one or more parts of the gear train. The gear case has a reservoir for holding the lubricant. At least one of the gears may move through the reservoir to lubricate the gear and consequently the gear mesh. At least one of the gears may be coupled to a shaft that projects out of the gear case. To prevent leakage from the reservoir or the gear case, the interface between the shaft(s) and the gear case is sealed.

The sealed interfaces, however, are often exposed to harsh conditions. For example, gear trains of locomotives are frequently exposed to large differences in temperature, humid environments, dry environments, abrasive dirt or grime, and/or challenging vibratory states. These conditions may cause a failure in the sealed interface thereby resulting in leakage of the lubricant. When an insufficient supply of lubricant is available for the gears, the machine may be susceptible to gear train or rolling element bearing damage that results in a locked axle condition. In the case of locomotives, locked axles may require the locomotive to be removed from service and sent to a facility for repair. Both the removal and repair of the locomotive may be time-consuming and costly. Furthermore, the lost productivity of the locomotive is also costly.

In addition to having a sufficient amount of lubricant, it is also desirable for the lubricant to have a sufficient quality during operation. For example, lubricants in a reservoir can become contaminated by water, metallic particles, and non-metallic particles. Contaminated fluids may lead to damaged parts or a decreased performance of the machine. In addition, the lubricant may age due to repetitive thermal and viscous cycles resulting in the loss of fluid properties such as viscosity.

Conventional methods of inspecting fluids of a machine include visual inspection of the fluid (e.g., dipsticks) or a sensor that is directly wired to a system. However, these methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

In addition to detecting the quantity and/or the quality of a liquid used by a machine, it may be desirable to obtain other information regarding an operative condition of a machine. For example, when an industrial machine is operating properly, the machine may have known or expected vibratory states. However, when a part of the machine is damaged or otherwise not operating properly, the vibrations of the machine may change. Therefore, it may be desirable to detect the vibrations of certain elements in a machine to monitor a health of the elements, other components of the machine, or the machine overall.

BRIEF DESCRIPTION

In accordance with an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

While multiple embodiments are disclosed, still other embodiments of the described subject matter will become apparent from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 11 is a cross-section of a wireless device utilizing the sensor of FIG. 5 in accordance with an embodiment.

FIG. 12 is a cross-section of a portion of a wireless device formed in accordance with an embodiment.

FIG. 13 is a front view of the wireless device of FIG. 13.

DETAILED DESCRIPTION

Figure 1:
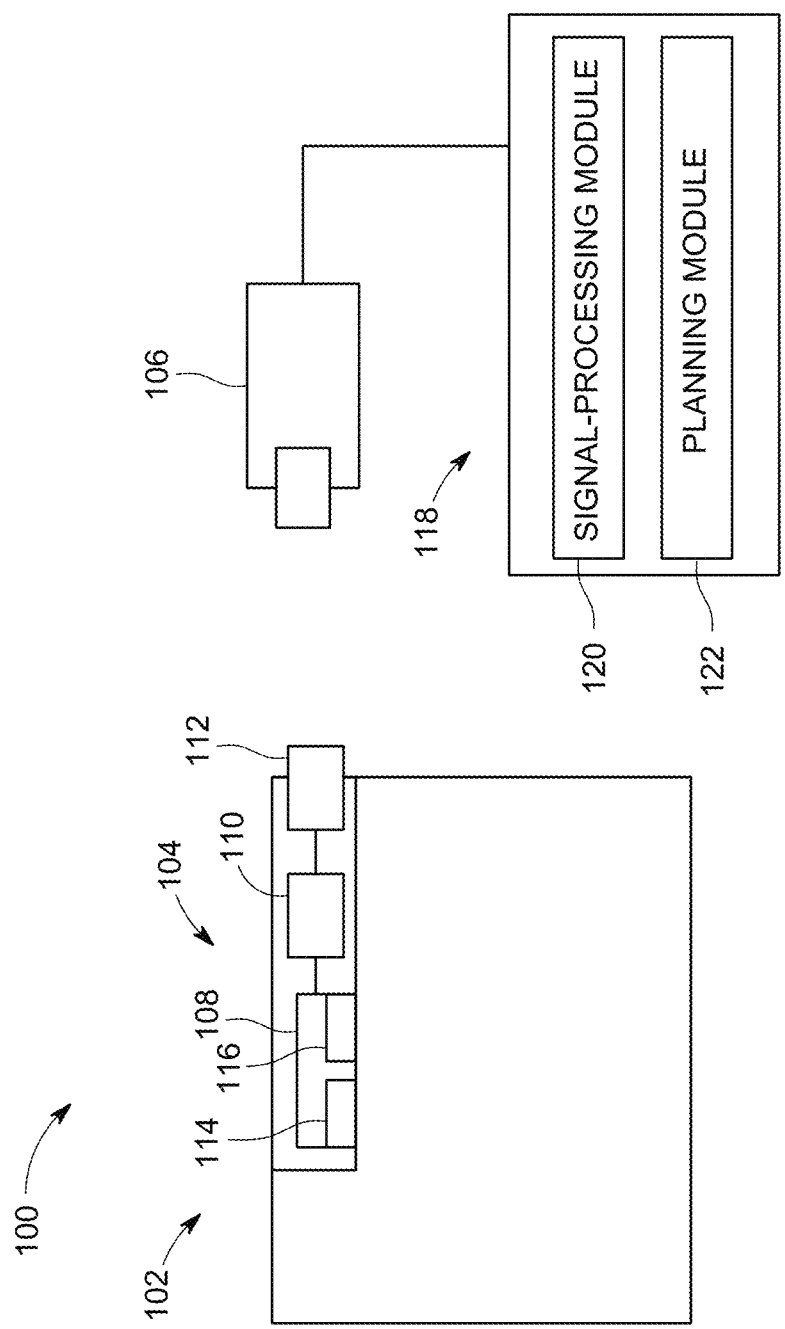
FIG. 1 is a schematic view of a system in accordance with an embodiment.

Embodiments described herein include various systems, assemblies, devices, apparatuses, and methods that may be used in a connection with obtaining one or more measurements of a machine. The measurement(s) may be representative or indicative of an operative condition of the machine. As used herein, an "operative condition of the machine" may refer to an operative condition of the machine as a whole or an operative condition of a component (e.g., element, assembly, or sub-system) of the machine. As used herein, the term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to locomotives or other rail vehicles, one or more measurements obtained from a locomotive or other rail vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may also comprise analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may also comprise analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may also be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a locomotive or other rail vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes). In some embodiments, the wireless device includes a storage unit (e.g., memory) where multiple measurements may be stored or logged. The wireless devices may also include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

The foregoing description of certain embodiments of the present inventive subject matter will be better understood when read in conjunction with the appended drawings. To the extent the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a schematic diagram of a system 100 formed in accordance with one embodiment. The system 100 is configured to obtain one or more measurements that are representative of an operative condition of a machine 102 or a component of the machine 102 (e.g., element, assembly, or sub-system of the machine 102). By way of example only, the machine 102 may be a motive machine or vehicle, such as an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In other embodiments, the machine is not configured to travel. For example, the machine may be a windmill or a power-generating turbine.

The operative condition may relate to a health or status of a designated component of the machine. Non-limiting examples of such components include a gearbox, a gear case, an air compressor, a turbo-charger, or a drive train. The measurement may be analyzed to determine, for example, that a component is damaged, is operating improperly (e.g., insufficiently or not at all), and/or is operating in a manner that will lead to or cause greater damage to the component or other component of the machine 102.

In particular embodiments, the operative condition is determined based on an amount or quality of liquid used by the machine 102 and/or a vibratory state of the machine 102. For instance, in some embodiments, the component may be a gear case that has a reservoir for storing a lubricant liquid. A low level or quantity of the liquid in the reservoir may indicate that the gear case is damaged. In particular, a low level or quantity may indicate that the gear case is leaking the liquid. In other embodiments, a component may have a particular vibratory state(s) when the component is operating properly. For example, a mechanical element may be configured to oscillate in a known or expected manner during operation. However, if the mechanical element is damaged or operating improperly, the mechanical element may have a different vibratory state.

As shown, the system 100 may include a wireless device 104 that is configured to wirelessly communicate data signals to a remote reader 106. The data signals may represent the measurement(s) obtained by the wireless device 104. To this end, the wireless device 104 may include a sensor 108, a processing unit 110, and a transmitter 112. The sensor 108 is configured to measure an operating parameter of the machine 102 and thereby obtain a measurement. In some embodiments, the sensor 108 includes a detector or transducer 114 and an activator 116. The activator 116 may be configured to provide a stimulus (e.g., sound waves, light, electric current, etc.) that causes a response by a component-of-interest or is affected by the component-of-interest. The detector 114 may be configured to detect the response that is caused by the stimulus or the affect that the component-of-interest has on the stimulus. For example, the stimulus may be sound waves that are detected to determine a liquid level (e.g., sonar). The stimulus may be light signals that are projected by a laser into a liquid to determine how much of the light signals are absorbed by the liquid. Another stimulus may be electric current. In other embodiments, the sensor 108 does not include an activator 116. Instead, the detector 114 may detect sound, vibrations, light, temperature, electrical properties, or other properties that occur in the environment without a stimulus provided by an activator.

The processing unit 110 is operably coupled to the sensor 108. The processing unit 110 is configured to receive measurement signals from the sensor 108 and process the measurement signals to provide data signals. The processing unit 110 may be an analog-to-digital converter (ADC). Alternatively or in addition to the ADC, the processing unit 110 may include a logic-based device that transforms the measurement signals into data signals. The data signals may then be configured to be transmitted to the reader 106 by the transmitter 112. For example, the processing unit 110 may be a computer processor, controller (e.g., microcontroller) or other logic-based device that performs operations based on one or more sets of instructions (e.g., software). The instructions on which the processing unit 110 operates may be stored on a tangible and non-transitory (e.g., not a transient signal) computer readable storage medium, such as a memory. The memory may include one or more types of memory, such as hard drives, flash drives, RAM, ROM, EEPROM, and the like. Alternatively, one or more of the sets of instructions that direct operations of the processing unit 110 may be hard-wired into the logic of the processing unit 110, such as by being hard-wired logic formed in the hardware of the processing unit 110.

The transmitter 112 is operably coupled to the processing unit 110 and is configured to wirelessly communicate the data signals to the reader 106. In some embodiments, the transmitter 112 is a transceiver that is configured to transmit the data signals and receive other signals, such as interrogation signals from the reader 106.

In some embodiments, the sensor 108, the processing unit 110, and the transmitter 112 are localized within and/or attached directly to the machine such that the sensor 108, the processing unit 110, and the transmitter 112 are proximate to each other and form a single device. The sensor 108, the processing unit 110, and the transmitter 112 may be in a localized spatial region of the machine that is separate from a computing system that controls operation of the machine. For example, the processing unit 110 and the transmitter 112 may be integrated with the same component such that the processing unit 110 and the transmitter 112 have fixed positions with each other. More specifically, the processing unit 110 and the transmitter 112 may be at least partially integrated onto a common component (e.g., circuit board) and/or positioned within a common container or housing that is coupled to the machine. The common container may not be coextensive with the machine and, instead, may be a separate component that is attached to or disposed within the machine-of-interest. By way of example only, some or all of the components of the processing unit 110 and the transmitter 112 may be located within 50 cm of each other, 20 cm of each other, 10 cm of each other or, more particularly, within 5 cm of each other.

In some embodiments, the processing unit 110 and the transmitter 112 may be part of a common RFID unit (e.g., tag, chip, card, and the like). Optionally, the sensor 108 may also be part of the common RFID unit. In other cases, the sensor 108 is separate from, but operably coupled to, the RFID unit and is only a short distance from the RFID unit. For example, the sensor 108 may be located within 50 cm or less of the RFID unit and communicatively coupled via wires or wireless communication. The RFID unit may be formed in accordance with RFID technology, which may include integrated circuit technology. For example, the RFID unit may be an electronic circuit that is capable of wireless communication. In some instances, the RFID unit may satisfy one or more established RFID standards and/or guidelines, such as standards and guidelines formed by the International Organization for Standardization (ISO), the International Electrotechnical Commission (IEC), ASTM International, the DASH7 Alliance, EPCglobal, the Financial Services Technology Consortium (FSTC).

In certain embodiments, the wireless device 104 is not physically electrically connected (e.g., not connected by wires or other conductors) to any of the one or more computers or other controller-based units in the machine. For example, in the context of trains, the wireless device 104 may be partially disposed within a reservoir and/or attached to a wall that defines the reservoir and is not physically electrically connected to the computing system that controls operation of the train. In such embodiments, the data signals from the wireless device 104 may be wirelessly transmitted from the wireless device 104 to, for example, a reader that is on-board or off-board. More specifically, the data signals may not be transmitted via wire/cables or other physical electrical connections. In one or more embodiments, at least portions of the processing unit 110 and the transmitter 112 may be directly connected to a wall that defines the reservoir (e.g., a wall that bears a pressure of and/or contacts the liquid in the reservoir) and/or to a structure immediately connected to the wall (e.g., support structure of the reservoir, gear case, or the like).

Various forms of wireless communication may be transmitted and received by the wireless device 104. For example, the transmitter 112 may be configured to receive and/or transmit radio signals, optical signals, signals based on sound, or signals based on magnetic or electric fields. In particular embodiments, the transmitter 112 is configured to receive and/or transmit radio signals in one or more radio frequencies. The wireless signals may be transmitted along a narrow radio band. In narrow band transmission, a single carrier frequency is used. Alternatively, the wireless signals may be transmitted within a spectrum of radio frequencies. For example, in spread spectrum transmission, the signals may be transmitted over a number of different radio frequencies within a radio band. The data signals may be modulated for transmission in accordance with any one of a number of modulation standards, such as frequency-hopping spread spectrum (FHSS), direct-sequence spread spectrum (DSSS), or chirp spread spectrum (CSS).

One wireless communication standard that may be used by embodiments described herein is IEEE 802.15.4. The IEEE 802.15.4 standard may operate within one of three frequency bands: (1) 868.0-868.6 MHz; (2) 902-928 MHz; or (3) 2400-2483.5 MHz. A number of channels may be used in each of the frequency bands. Embodiments may also use frequency bands that are associated with RFID technology, such as 120-150 kHz, 13.56 MHz, 865-868 MHz, 902-028 MHz, 2450-5800 MHz, or 3.1-10 GHz. Ultra wideband (UWB) may also be used.

In some embodiments, a transmission range of the data signals and/or the signals from the reader 106 is about 0-10 meters or from about 0-20 meters. In other embodiments, the transmission range may be greater, such as up to 100 meters or more.

Various embodiments may be based on or consistent with radio frequency identification (RFID) technology. For example, the wireless device 104 may be a passive sensor, a semi-passive sensor, or an active sensor. A passive sensor may not include a power source. Instead, the power may be based on inductive coupling or backscatter coupling with the reader. A semi-passive sensor may include a power source for only designated functions. For example, a battery and/or an energy harvesting device may be used to increase the transmission distance. The passive and semi-passive sensors may be particularly suitable for when the reader is present (e.g., within transmission range so that the sensors can be powered by the reader). An active sensor may include a power source for powering multiple functions (e.g., detection, reception, and transmission). Active sensors may be used in embodiments in which the reader is configured to only receive data signals and not transmit interrogation signals.

The reader 106 may be operably connected to a control system 118 having a signal-processing or diagnostic module 120 and, optionally, a planning module 122. Like the processing unit 110, the modules 120, 122 may be a computer processor, controller (e.g., microcontroller), or other logic-based device that performs operations based on one or more sets of instructions. The instructions on which the modules 120, 122 operates may be stored on a tangible and non-transitory (e.g., not a transient signal) computer readable storage medium, such as a memory. Alternatively, one or more of the sets of instructions that direct operations of the modules 120, 122 may be hard-wired into the logic of the modules 120, 122. The module 120, 122 may be located on separate devices (e.g., separate processors) or may be located on common processor.

The signal-processing module 120 may be configured to determine, based on the data signals received by the reader 106, whether the machine 102 is operating improperly. The signal-processing module 120 may determine whether the machine 102 is operating properly or improperly by analyzing the data signals that are representative of the measurements. For example, the signal-processing module 120 may use a look-up table or other databases that provides acceptable ranges of operation. If the measurement based on the data signals is not within the range, the signal-processing module 120 may determine that the machine 102 is not operating properly. In some cases, based on the measurement(s), the signal-processing module 120 may be able to determine whether a particular component of the machine 102 is in need of maintenance, repair, or replacement or whether the machine 102 requires an overhaul of a subsystem.

Based on the measurement(s), the signal-processing module 120 may request that an operating plan be generated by the planning module 122. The operating plan may be configured to improve the performance of the machine 102 and/or to limit the performance of the machine 102 to prevent damage or additional damage. The operating plan may include instructions for replacing, maintaining, modifying, and/or repairing a designated component or components of the machine 102.

The operating plan may be based on the operative condition, which is at least partially a function of the measurement(s) obtained. For instance, if a capacitive measurement indicates that the liquid level is less than sufficient, but a substantial amount remains in the gear case, then the operating plan may include instructions for refilling the liquid at a first facility and then resealing the gear case at a second facility located further away. However, if a capacitive measurement indicates that the liquid level quickly reduced to little or no measurable amount of liquid, then the operating plan may instruct that the gear case be replaced at a designated facility.

In the context of a locomotive or other vehicle, the operating plan may include instructions for controlling tractive and/or braking efforts of the vehicle. In particular, the operating plan may be partially based on the measurements of the operative condition of the machine. The instructions may be expressed as a function of time and/or distance of a trip along a route. In some embodiments, travel according to the instructions of the operating plan may cause the vehicle to reduce a stress on a component-of-interest of the machine than the component would typically sustain during normal operation. For example, the operating plan may instruct the vehicle to reduce horsepower delivered to an axle, to intermittently drive the axle, or to disable the axle altogether. The vehicle may be autonomously controlled according to the operating plan or the instructions of the operating plan may be presented to an operator of the vehicle so that the operator can manually control the vehicle according to the operating plan (also referred to herein as a "coaching mode" of the vehicle).

In some embodiments, the operating plan that is generated when it is determined that the machine is operating improperly is a "revised" operating plan that supersedes or replaces another operating plan. More specifically, due to the newly acquired measurements, the control system may determine that the currently-implemented operating plan should be modified and, as such, may generate a revised operating plan to replace the other.

Operating plans may be optimized to achieve designated goals or parameters. As used herein, the term "optimize" (and forms thereof) are not intended to require maximizing or minimizing a characteristic, parameter, or other object in all embodiments described herein. Instead, "optimize" and its forms may include increasing or decreasing (as appropriate) a characteristic, parameter, or other object toward a designated or desired amount while also satisfying other conditions. For example, optimized stress levels on a component may not be limited to a complete absence of stress or that the absolute minimum amount of stress. Rather, optimizing the stress level may mean that the stress is controlled, while also satisfying other conditions (e.g., speed limits, trip duration, arrival time). For example, the stress sustained by a component may be controlled so that the vehicle may arrive at its destination without the component being severely damaged.

The planning module 122 is configured to use at least one of vehicle data, route data (or a route database), part data, or trip data to generate the operating plan. The vehicle data may include information on the characteristics of the vehicle. For example, when the vehicle system is a rail vehicle, the vehicle data may include a number of rail cars, number of locomotives, information relating to an individual locomotive or a consist of locomotives (e.g., model or type of locomotive, weight, power description, performance of locomotive traction transmission, consumption of engine fuel as a function of output power (or fuel efficiency), cooling characteristics), load of a rail vehicle with effective drag coefficients, vehicle-handling rules (e.g., tractive effort ramp rates, maximum braking effort ramp rates), content of rail cars, lower and/or upper limits on power (throttle) settings, etc.

Route data may include information on the route, such as information relating to the geography or topography of various segments along the route (e.g., effective track grade and curvature), speed limits for designated segments of a route, maximum cumulative and/or instantaneous emissions for a designated segment of the route, locations of intersections (e.g., railroad crossings), locations of certain track features (e.g., crests, sags, curves, and super-elevations), locations of mileposts, and locations of grade changes, sidings, depot yards, and fuel stations. The route data, where appropriate, may be a function of distance or correspond to a designated distance of the route.

Part data may include, for example, historical data or proprietary data regarding the lifetime operability of a component. The data may include baseline data for a designated speed and/or load on the machine. Additional factors may be part of the baseline data. For example, if the lubricant has a designated quantity in the gear case, the part data may include data from identical components that operated with an approximately equal lubricant level. The data may include how long the component is capable of operating at a designated speed.

Trip data may include information relating to a designated mission or trip, such as start and end times of the trip, start and end locations, route data that pertains to the designated route (e.g., effective track grade and curvature as function of milepost, speed limits), upper cumulative and/or instantaneous limits on emissions for the trip, fuel consumption permitted for the trip, historical trip data (e.g., how much fuel was used in a previous trip along the designated route), desired trip time or duration, crew (user and/or operator) identification, crew shift expiration time, lower and/or upper limits on power (throttle) settings for designated segments, etc. In one embodiment, the planning module 122 includes a software application or system such as the Trip Optimizer™ system developed by General Electric Company.

Figure 2:
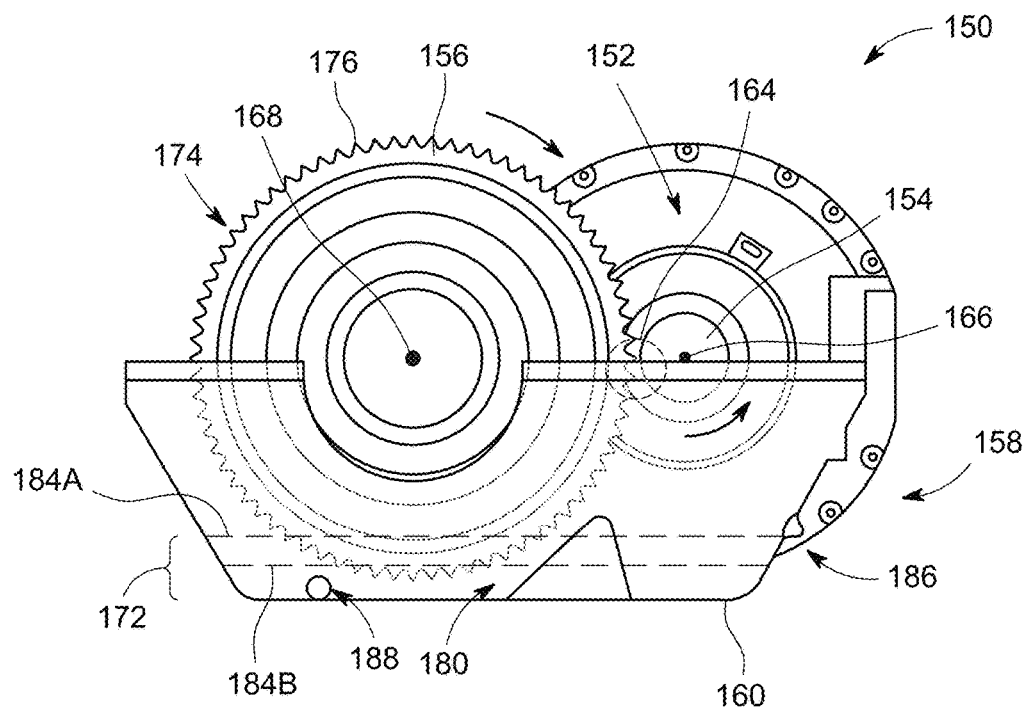
FIG. 2 is a side view of a drive train in accordance with an embodiment.
Figure 3:
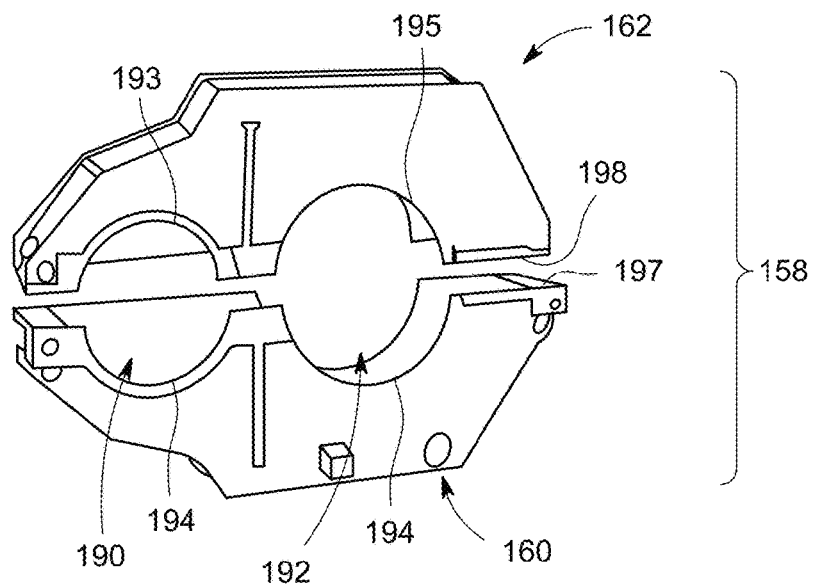
FIG. 3 is a partially exploded view of a gear case that may be used by the drive train of FIG. 2.

FIG. 2 is a side view of a drive train (or final drive) 150 in accordance with one embodiment. The drive train 150 includes a traction motor 152, a first (or pinion) gear 154, a second gear 156, and a base portion or shell 160 of a gear case 158. A top portion or shell 162 of the gear case 158 is shown in FIG. 3. As shown in FIG. 2, the first gear 154 and the second gear 156 engage each other at a gear mesh 164. During operation of the drive train 150 the traction motor 152 drives the first gear 154 by rotating an axle (not shown) coupled to the first gear 154 about an axis of rotation 166. The first gear 154 may be rotated, for example, in a counter-clockwise direction as viewed in FIG. 2. Due to the engagement at the gear mesh 164, the first gear 154 rotates the second gear 156 in a clockwise direction about an axis of rotation 168. The second gear 156 is coupled to an axle (not shown) that rotates with the second gear 156. The axle of the second gear 156 is coupled to wheels (not shown) that are rotated with the axle. The wheels engage a surface (e.g., rails or tracks) to move the machine.

The gear case 158 includes a reservoir 172 that is configured to hold a lubricant liquid 180 (e.g., oil). The gear case 158 has a fill or inlet port 186 and a drain or outlet port 188. The liquid 180 may be provided to the reservoir 172 through the fill port 186 and drained through the drain port 188.

As shown in FIG. 2, the second gear 156 has teeth 176 along an edge 174 of the second gear 156. When the liquid 180 is held within the gear case 158, the liquid 180 may have a fill level 184. FIG. 2 illustrates a first fill level 184A and a second fill level 184B. The second fill level 184B is lower than the first fill level 184A. In some embodiments, when the drive train 150 is operating properly, the quantity of the liquid 180 correlates to the first fill level 184A such that the edge 174 of the second gear 156 is sufficiently submerged within or bathed by the liquid 180. However, when the fill level is lowered to, for example, the fill level 184B, the edge 174 and teeth 176 may be insufficiently lubricated. Such circumstances may occur when the gear case 158 has a leak.

FIG. 3 is a partially exploded view of the gear case 158 and illustrates the base and top portions 160, 162 before the base and top portions 160, 162 are coupled to the drive train to surround the first and second gears 154, 156. As shown, the gear case 158 may include first and second gear-receiving openings 190, 192 that are sized to receive the first and second gears 154, 156 (FIG. 2), respectively. The gear-receiving openings 190, 192 may be defined by opening edges 193-196 and the base and top portions 160, 162 may engage each other along case edges 197, 198.

When the drive train 150 is fully constructed and operational, the opening edges 193-196 engage the portions of the drive train 150 along sealable interfaces. The case edges 197, 198 may also be coupled to each other along a sealable interface. During operation of the drive train 150, however, the interfaces may become damaged or worn such that the interfaces are no longer sufficiently sealed. For example, when the drive train 150 is part of a locomotive, the opening edges 193-196 or the case edges 197, 198 may become worn, damaged, or separated such that the liquid 180 is permitted to escape the reservoir 172. Accordingly, the amount of liquid 180 may reduce such that the fill level 184 (FIG. 2) lowers.

Embodiments described herein may be configured to detect that the amount of liquid 180 has reduced. In addition, due to the wear, damage, or separation of the base and top portions 160, 162, the gear case 158 (or portions thereof) may exhibit different vibratory characteristics. For example, a gear case that is sufficiently sealed with respect to the drive train 150 and has a sufficient fill level 184 may exhibit a first vibratory state when the drive train 150 is driven at a first speed. However, a gear case that is insufficiently sealed with respect to the drive train 150 and/or has an insufficient fill level 184 may exhibit a second vibratory state that is different than the first vibratory state when the drive train 150 is driven at the first speed. Embodiments described herein may be configured to detect and measure the different vibratory states. In certain embodiments, a wireless device, such as those described herein, is at least partially disposed within the reservoir 172 and/or directly attached to a portion of the gear case 158. For example, at least a portion of the wireless device 158 may be directly secured or affixed to a wall of the gear case 158, such as the wall that defines the reservoir 172. In some embodiments, the wireless device 172 is not physically electrically connected to other components of the machine, such as a computing system that controls operation of the machine.

In addition to liquid level and vibrations, embodiments may be configured to detect other characteristics. For example, other measurements may relate to a quality (e.g., degree of contamination) of the liquid. Contaminants may include water, metallic particles, and/or non-metallic particles. Furthermore, embodiments are not limited to the drive train or a gear case of the driver train. For example, measurements that may be obtained for a drive train may also be obtained for a turbo-charger, an air compressor, an engine, and the like. Other components of a machine may also be measured by wireless devices described herein.

Figure 4:
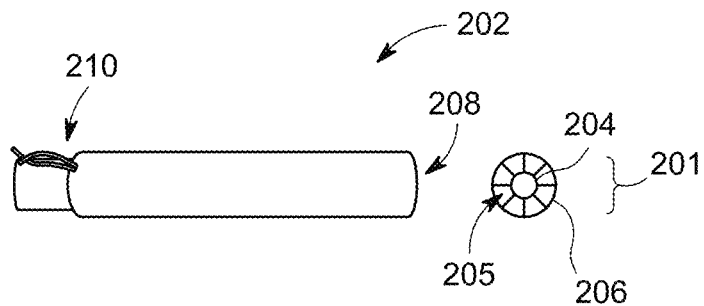
FIG. 4 is a side view of a capacitive-type sensor in accordance with an embodiment.
Figure 5:
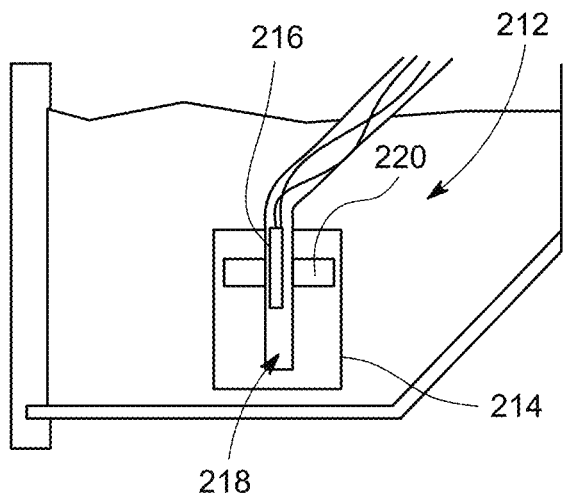
FIG. 5 is a schematic view of a magnetic float/reed switch sensor in accordance with an embodiment.
Figure 6:
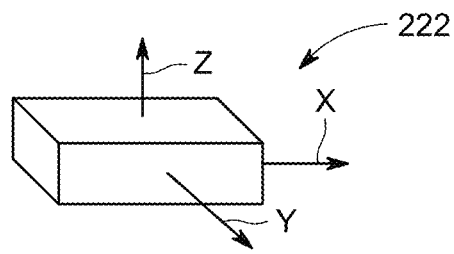
FIG. 6 is a schematic view of an accelerometer in accordance with an embodiment.

FIGS. 4-6 illustrate sensors 202, 212, 222, respectively. The sensors, which may also be referred to as transducers, may be a portion of the wireless devices described herein. Each of the sensors may be configured to measure (e.g., detect) a designated property or characteristic in the environment proximate to the sensor and provide a signal that is representative of the measured property or characteristic. The signal provided by the sensor may be the measurement.

Various types of measurements may be obtained by the sensors. Some non-limiting examples include a capacitance of a liquid, a temperature of a liquid and/or temperatures of certain parts of a machine, a fluid conduction of a liquid, a dielectric constant of a liquid, a dissipation factor of a liquid, an impedance of a liquid, a viscosity of a liquid, or vibrations of a mechanical element. A measurement may be directly obtained (e.g., temperature) by the sensor, or a designated measurement may be obtained after using information provided by the sensor to calculate the designated measurement. For example, the viscosity of the liquid may be calculated based on multiple level measurements obtained by a sensor.

Embodiments may include a single wireless device that is configured to measure and communicate only a single type of measurement (e.g., capacitance). However, in some embodiments, a single wireless device may be configured to measure and communicate multiple types of measurements (e.g., capacitance of the liquid, temperature of the liquid, temperature of the sensor, shock and/or vibration of the gear case, etc.). In such embodiments, the wireless device may have multiple sensors.

The sensor 202 is configured to measure a capacitance of a liquid, such as a lubricant in a tank (e.g., gear case). The sensor 202 is hereinafter referred to as a capacitive level probe 202. For reference, a cross-section 201 of the level probe 202 is also shown in FIG. 4. The level probe 202 extends lengthwise between a leading end 208 and a trailing end 210. The level probe 202 includes an inner or measurement electrode 204 and an outer or reference electrode 206. As shown, a space 205 exists between the inner and outer electrodes 204, 206. A capacitance of the material that exists within the space 205, such as a combination of a liquid and gas, may be measured by the level probe 202. In some embodiments, a wall of the tank that holds the liquid may be used as the reference electrode.

The level probe 202 is configured to be immersed into the liquid (e.g., oil) held by the tank. For example, the leading end 208 may be inserted into the liquid. As the leading end 208 is submerged, the liquid may flow into the space 205 thereby changing a ratio of liquid to gas within the space 205. As such, the measured capacitance changes as the level of the liquid within the space 205 changes. If the liquid is a lubricant, the measured value of capacitance decreases as an amount or level of the liquid decreases. As an amount or level of the liquid increases, the measured value of capacitance also increases.

The level probe 202 may also be configured to determine a quality of the liquid. More specifically, the level probe 202 may detect an amount or percentage of contaminations in the liquid based on capacitance measurements. For example, contaminant detection may be based on a dissipation factor of a dielectric of the liquid. In general, the dissipation factor is a function of an applied frequency, a liquid temperature, a composition of the liquid (e.g., the desired composition of the liquid), and contaminants. The dissipation factor may be substantially independent of the base capacitance or liquid level.

In some cases, movement of the machine may cause a displacement of the liquid which may introduce an error in the measurements. Accordingly, in some embodiments, the level probe 202 is only activated when the machine or component thereof is at rest (e.g., inactive). To this end, an accelerometer or other inertial type sensor may be part of or operably coupled to the wireless device that includes the level probe 202. The accelerometer may determine that the machine is in an inactive or stationary state such that measurements may be obtained by the level probe 202.

As shown in FIG. 5, the sensor 212 includes a body float 214 and a reed switch 216. The body float 214 includes a cavity 218 that is sized and shaped to receive the reed switch 216. The body float 214 is configured to float along the reed switch 216 (e.g., vertically) based on a level of the liquid in the reservoir. The body float 214 includes a permanent magnet 220, and the reed switch 216 includes a magnetically actuated switch or switches (not shown). As the body float 214 moves up and down, the permanent magnet 220 may activate or deactivate the switch (e.g., close or open a circuit, respectively, in the reed switch 216). The activated switch indicates that the body float 214 is at a designated level and, consequently, that the liquid is at a designated level.

As described above, one or more embodiments may also include a sensor that is an accelerometer. FIG. 6 illustrates one such sensor, which is referenced as an accelerometer 222. In some embodiments, the accelerometer 222 is a micro-electro-mechanical system (MEMS) tri-axis accelerometer. The accelerometer 222 may be used for a variety of functions. For example, the accelerometer 222 may be coupled to a mechanical element, such as a tank, and determine whether the mechanical element has remained stationary for a designated amount of time. In some embodiments, other measurements (e.g. liquid level) may be obtained only after it has been determined that the mechanical element has remained stationary for the designated amount of time.

Alternatively or additionally, the accelerometer 222 may be configured to detect vibratory states experienced by the mechanical element. For example, the accelerometer 222 may be configured to obtain numerous shock and vibrations measurements per second in each of x-, y-, and z-axes. For example, the accelerometer 222 may be able to log hundreds or thousands of data points per second in each of the x-, y-, and z-axes.

Figure 7:
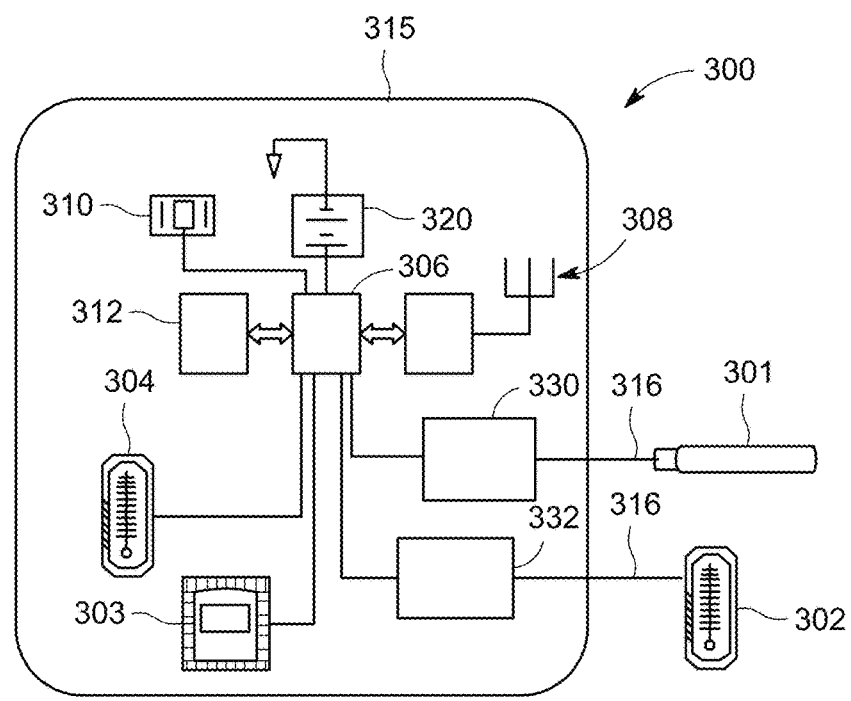
FIG. 7 is a schematic diagram of a wireless device formed in accordance with an embodiment.

FIG. 7 is a schematic diagram of a wireless device 300 formed in accordance with one embodiment. The wireless device 300 includes sensors 301-304, a processing unit 306 (e.g., microprocessor), a transmitter 308, an internal clock 310 (e.g., real-time clock crystal), and a memory 312 (e.g., non-volatile memory). The wireless device 300 has a device body 315, which may include a printed circuit board (PCB) or a die (e.g., semiconductor wafer) in some embodiments. In the illustrated embodiment, the device body 315 includes the sensors 303, 304, the processing unit 306, the transmitter 308, the internal clock 310, and the memory 312. In alternative embodiments, however, the wireless device 300 may have multiple bodies (e.g., multiple dies) that are coupled to each other and/or the components described herein may be separate from the device body 315. The sensors 301 and 302 may be operably coupled to the device body 315 through, for example, wires 316. In other embodiments, the sensors 301, 302 are wirelessly coupled to the device body 315.

The sensor 301 may be a level probe, such as the level probe 202 described with respect to FIG. 4. The sensor 301 is configured to be inserted into a liquid (e.g., lubricant) of a machine. The sensor 302 may be a thermometer that is configured to obtain a temperature of the liquid. The sensor 303 is an accelerometer, such as the accelerometer 222 (FIG. 6), and the sensor 304 is another thermometer that is configured to determine a temperature of the device body 315 of the wireless device 300. Each of the sensors 301-304 is communicatively coupled to the processing unit 306 and configured to communicate signals to the processing unit 306. The signals may be representative of a property or characteristic detected by the sensor.

The processing unit 306 may be configured to store or log data (e.g., data based on the signals obtained from the sensors) in the memory 312. In some embodiments, the processing unit 306 is configured to query the sensors 301-304 to request measurements from the sensors 301-304. The queries may occur at predetermined times or when a designated event occurs. For example, the queries may occur once an hour as determined by the internal clock 310 until, for example, the wireless device 300 is interrogated by a reader (not shown). At such an event, the processing unit 306 may query the sensors 301-304 for numerous data points. For example, the data points may be provided almost continuously after interrogation. The processing unit 306 may also receive data from the memory 312. The data received from the sensors 301-304 and/or the memory 312 may be transformed into data signals that are communicated by the transmitter 308 to the reader.

The wireless device 300 may be characterized as an active or semi-passive device. For example, the wireless device 300 may include a power source 320, such as a battery (e.g., lithium thionyl chloride battery) and/or kinetic energy harvesting device. The wireless device 300 may utilize the power source 320 to increase the transmission range of the transmitter 308. In such embodiments, the reader may be located tens or hundreds of meters away from the wireless device 300. In addition to the transmitter 308, the power source 320 may be used to supply power to other components of the wireless device 300, such as the sensors 301-304 or the processing unit 306.

Figure 8:
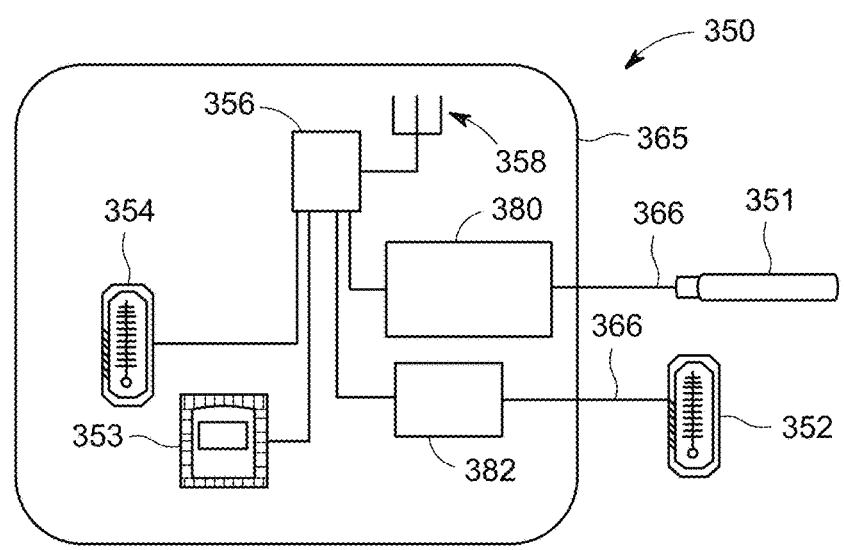
FIG. 8 is a schematic diagram of a wireless device formed in accordance with an embodiment.

FIG. 8 is a schematic diagram of a wireless device 350 formed in accordance with one embodiment. The wireless device 350 may be a passive device such that the wireless device 350 is powered by inductive or backscatter coupling with the reader (or some other non-internal power source). As shown, the wireless device 350 includes sensors 351-354, a processing unit 356, and a transmitter 358. The wireless device 300 has a device body 365 that includes, in the illustrated embodiment, the sensors 353, 354, the processing unit 356, and the transmitter 358. The device body 365 may be formed by integrated circuit technology. For example, the device body 365 may include one or more printed circuit boards (PCBs). The sensors 351 and 352 may be operably coupled to the device body 365 through, for example, wires 366. Similar to the wireless device 300 (FIG. 7), the sensors 351-354 may be a level probe, external thermometer, an accelerometer, and an internal thermometer, respectively.

In some embodiments, the processing unit 356 executes fewer calculations or conversions of the signals from the sensors 351-354 than the processing unit 306 (FIG. 7). For example, the processing unit 356 may be an ADC that converts the analog signals from the sensors 351-354 to digital signals. The digital signals may be the data signals that are then transmitted by the transmitter 358. In the illustrated embodiment, the processing unit 356 may only query the sensors 351-354 after being interrogated by a reader (not shown). More specifically, the interrogation signals from the reader may power the processing unit 356 to query the sensors 351-354 and transmit the data signals.

Figure 9:
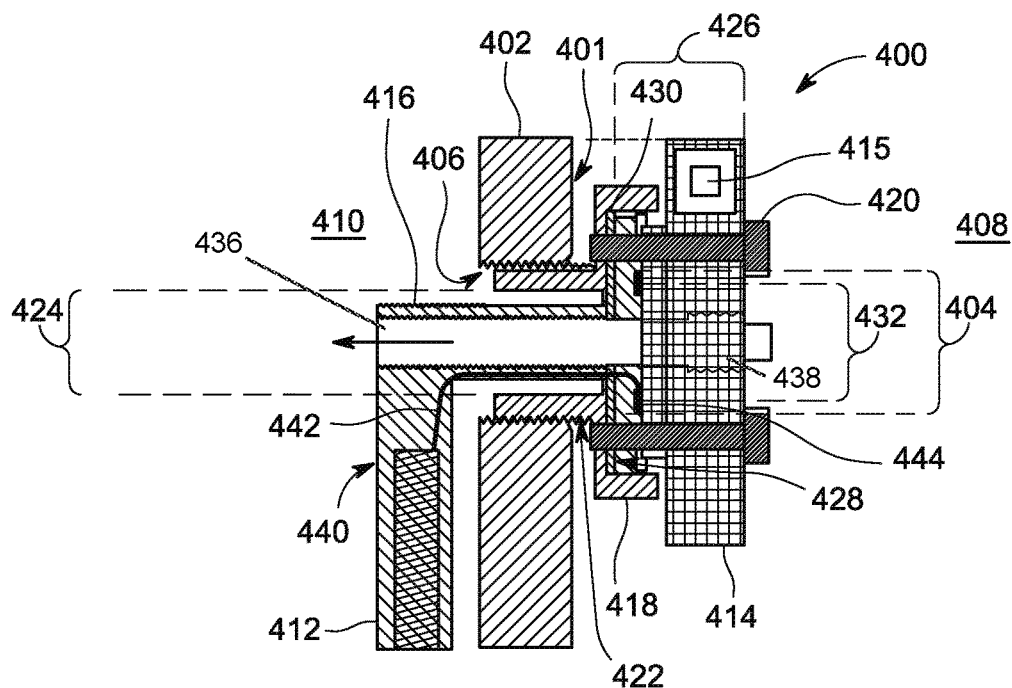
FIG. 9 is a cross-section of a portion of a wireless device utilizing the sensor of FIG. 4 in accordance with an embodiment.

FIG. 9 is a cross-section of a portion of a wireless device 400 attached to a wall 402 of a tank 401. The tank 401 may be part of a machine, such as a locomotive or other machines described herein. The tank 401 is configured to have a reservoir 410 for holding a liquid (not shown), such as a lubricant. The reservoir 410 is accessed through a fill port 404 of the wall 402 that is defined by interior threads 406 of the wall 402 as shown in FIG. 9. The fill port 404 provides access from an exterior 408 of the tank 401 to the reservoir 410.

As shown, the wireless device 400 includes a sensor 412, a device body 414, and an intermediate cable portion 416 that joins the sensor 412 and the device body 414. The wireless device 400 also includes a coupling component 418 that is configured to be secured to the device body 414 through, for example, fasteners 420 and attached to the wall 402. In the illustrated embodiment, the coupling component 418 includes threads 422 that complement and are configured to rotatably engage the threads 406 of the wall 402. However, in other embodiments, different methods of attaching the coupling component 418 to the tank may be used, such as latches, interference fits (e.g., plugs), and/or adhesives.

To assemble the wireless device 400, the coupling component 418 may be rotatably engaged to the wall 402. The sensor 412 and the cable portion 416 may be inserted through an opening 424 of the coupling component 418 and the fill port 404. As shown, the coupling component 418 has a mating face 428 that faces in a direction away from the wall 402. The cable portion 416 has a mating end 426 that is located in the exterior 408 of the tank 401 and may be pressed toward the mating face 428 with a gasket 430 located therebetween. The device body 414 has a cable opening 432 that receives an end of the cable portion 416. The device body 414 may be secured to the cable portion 416 and the coupling component 418 using the fasteners 420. As shown, the cable portion 416 includes a fill channel 436 that permits access to the reservoir 410. During operation, the fill channel 436 may be closed with a plug 438 at the mating end 426 of the cable portion 416.

The sensor 412 may be similar or identical to the level probe 202 described with respect to FIG. 4. For example, a trailing end 440 of the sensor 412 is shown in FIG. 9. The trailing end 440 is coupled to wires 442 that communicatively couple the sensor 412 to the device body 414. In other embodiments, the sensor 462 may be similar or identical to the sensor 212 (FIG. 5). The cable portion 416 is configured to surround and protect the wires 442 from the surrounding environment. As shown, the wires 442 terminate at a contact ring 444 along the device body 414. The sensor 412 is configured to transmit signals to the device body 414 through the wires 442 and the contact ring 444. The device body 414 is configured to process and transmit data signals that represent measurements obtained by the sensor 412. The device body 414 may include an integrated circuit unit 415. Although not shown, the integrated circuit unit 415 of the device body 414 may have a processing unit, power source, internal clock, additional sensors, and/or a transmitter, such as those described above. In some embodiments, the integrated circuit component 415 is formed as an RFID unit.

Figure 10:
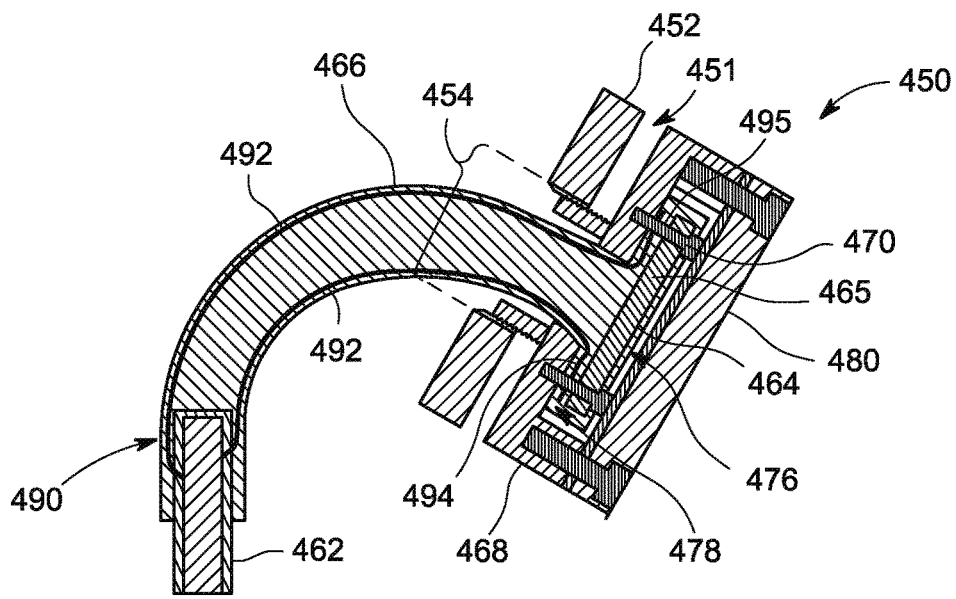
FIG. 10 is a cross-section of a portion of a wireless device utilizing the sensor of FIG. 4 in accordance with an embodiment.

FIG. 10 is a cross-section of a portion of a wireless device 450, which is also configured to be coupled to a wall 452 of a tank 451. The wireless device 450 may include similar features as the wireless device 400 (FIG. 9). For example, the wireless device 450 includes a sensor 462, a device body 464, and an intermediate cable portion 466 that joins the sensor 462 and the device body 464. The wireless device 450 also includes a coupling component 468 that is configured to be secured directly to the device body 464 and the cable portion 466 through fasteners 470. In the illustrated embodiment, the coupling component 468 is rotatably engaged to the wall 452 in a similar manner as the coupling component 418 (FIG. 9). However, other methods of attaching the coupling component 468 to the wall may be used.

To assemble the wireless device 450, the coupling component 468 may be rotatably engaged to the wall 452. The sensor 462 and the cable portion 466 may be inserted through the coupling component 416 and a fill port 454 of the wall 452. The device body 464 may be encased within a mating end 476 of the cable portion 466. As shown, the coupling component 468 has a mating face 478 that faces in a direction away from the wall 452. Accordingly, the cable portion 466 and the device body 464 may be secured to the coupling component 468 using the fasteners 470. A cover body 480 may then be positioned over the cable portion 466 to hold the device body 464 between the cover body 480 and the coupling component 468. Unlike the wireless device 400, the cable portion 466 does not include a fill channel that permits access to the reservoir.

The sensor 462 may be similar or identical to the level probe 202 described with respect to FIG. 4. For example, a trailing end 490 of the sensor 462 is shown in FIG. 10. The trailing end 490 is coupled to wires 492 that communicatively couple the sensor 462 to the device body 464. In other embodiments, the sensor 462 may be similar or identical to the sensor 212 (FIG. 5). As shown, the wires 492 terminate at contacts 494, 495 that are coupled to the device body 464. The device body 464 may include an integrated circuit component 465, which, in the illustrated embodiment, is a RFID unit. The sensor 462 is configured to transmit signals to the integrated circuit component 465 through the wires 492. Like the integrated circuit component 415, the integrated circuit component 465 is configured to process and transmit data signals that represent measurements obtained by the sensor 462. The integrated circuit component 465 may include a processing unit, power source, internal clock, additional sensors, and/or a transmitter, such as those described above.

FIG. 11 is a cross-section of a portion of a wireless device 500. The wireless device 500 may be similar to the wireless device 400 (FIG. 9) and the wireless device 450 (FIG. 10).

However, as shown in FIG. 11, the wireless device 500 utilizes a sensor 502 that may be similar to or identical to the sensor 212 (FIG. 5). The wireless device 500 also includes a coupling component 504 that is configured to attach to a wall 506 of a tank 508, which is a gear case in the illustrated embodiment. The coupling component 504 may be similar to the coupling components described above. For example, the coupling component 504 may rotatably engage the wall 506.

Also shown, the wireless device 500 includes a device body 530 that is operably coupled to the sensor 502 through a base support 510 and an intermediate beam 512. The base support 510 is disposed within an opening 514 of the coupling component 504. The beam 512 extends between and joins the sensor 502 and the base support 510. The beam 512 may be fabricated from, for example, stainless steel and is configured to provide a passageway 516 for wires 518 that communicatively couple the device body 530 and the sensor 502.

The base support 510 includes a mating face 520 that faces away from the tank 508. The mating face 520 has contacts 524, 525 thereon. The contact 524 may be a contact pad, and the contact 525 may be a ring contact that extends around the contact pad. A device body 530 is configured to be rotatably engaged to the coupling component 504. The device body 530 includes a mounting surface 532 that faces the mating face 520 and has corresponding contacts that are configured to engage the contacts 524, 525. More specifically, when the device body 530 is rotated to engage the coupling component 504, the mounting surface 532 of the device body 530 may advance toward the mating face 520 so that the contacts of the device body 530 press against and engage the contacts 524, 525.

Accordingly, the device body 530 may be communicatively coupled to the sensor 502. Similar to the device bodies described above, the device body 530 may include an integrated circuit component 515 having a processing unit and a transmitter (not shown). Optionally, the integrated circuit component 515 may also include a memory, an internal clock, and one or more other sensors. The integrated circuit component 515 may transform the signals from the sensor 502 (or memory or other sensors) into data signals. The data signals may then be transmitted to a reader (not shown). In some embodiments, the integrated circuit component 515 is formed as an RFID unit.

FIG. 12 is a cross-section and FIG. 13 is a front view, respectively, of a portion of a wireless device 550. The wireless device 550 may include a sensor (not shown) and a device body 552 that are communicatively coupled through wires 554. The sensor may be similar to the sensor 202 (FIG. 4) or the sensor 212 (FIG. 5). The device body 552 is secured to a faceplate 556 that is coupled to an exterior surface of a tank 560 (FIG. 13). FIGS. 12 and 13 illustrate an embodiment in which no electrical contacts are required along the device body 552 to electrically join the sensor. Instead, wires 554 (FIG. 12) from the sensor may extend through potting 562 that mechanically couples the sensor to the tank 560. Like the wireless device 400 (FIG. 9), the wireless device 550 may permit access to a fill port 566 through a plug 568. Although not shown, the device body 552 may include an integrated circuit component, such as those described above, that processes data signals and transmits data signals. The integrated circuit component may be an RFID unit that is directly coupled to one of the wires 554.

Figure 14:
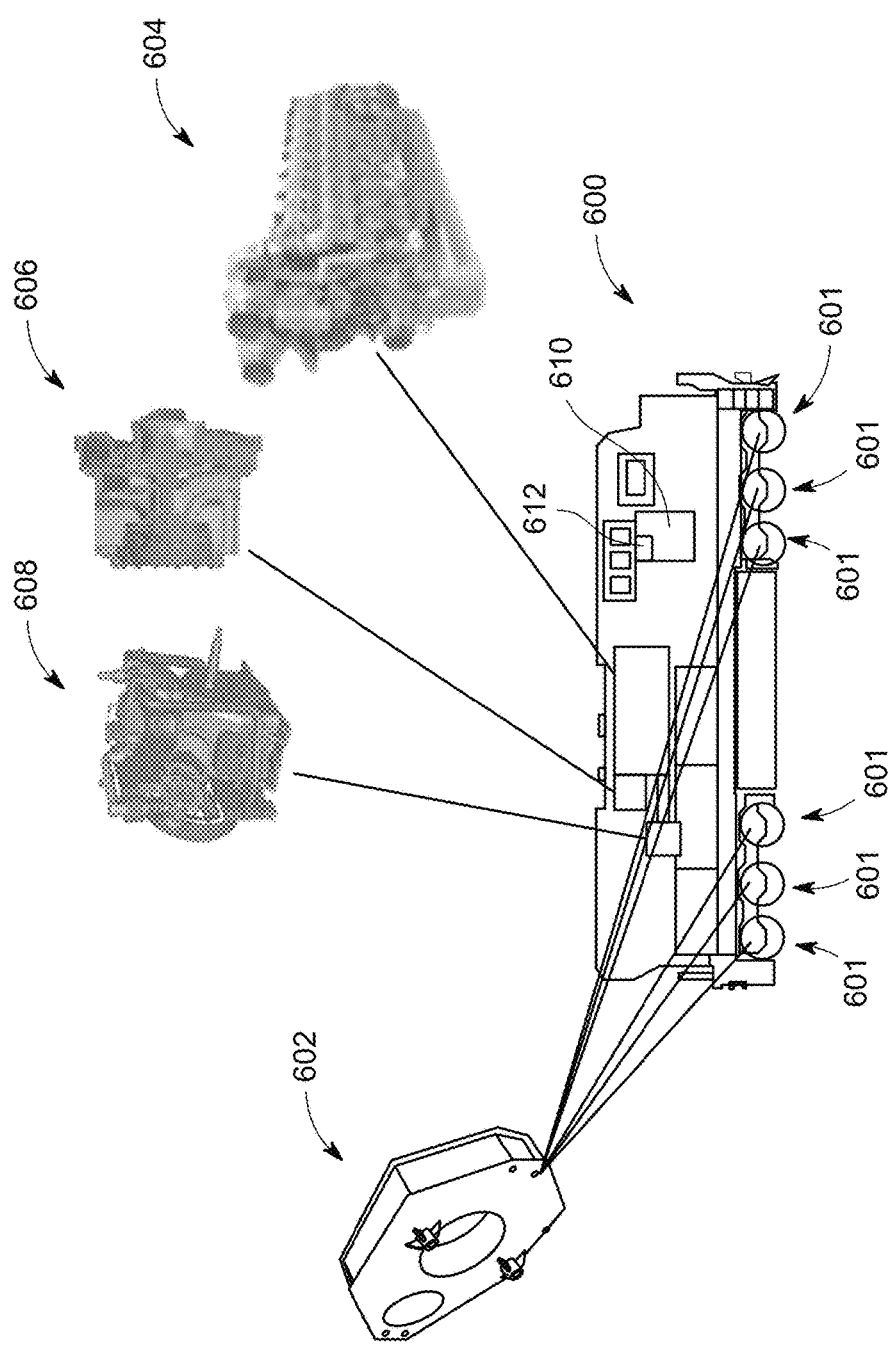
FIG. 14 is a schematic view of a locomotive and illustrates a plurality of components of the locomotive in accordance with an embodiment.

FIG. 14 is a schematic view of a locomotive 600 and illustrates a plurality of components of the locomotive 600 that may include one or more wireless devices, such as the wireless devices described herein. For example, the locomotive 600 may include a plurality of drive trains 601 that each has a gear case 602. The locomotive 600 may also include an engine 604, a turbo-charger 606 operably coupled to the engine 604, and an air compressor 608. Each of the components may have one or more of the wireless devices described herein operably coupled thereto. For example, the gear cases 602 and the engine 604 may have at least one of the wireless devices 202, 212, 222, 400, 450, 500, or 550 described above. In particular, each of the gear cases 602 and the engine 604 may have a reservoir that includes a liquid lubricant. The turbo-charger 606 and the air compressor 608 may use, for example, an accelerometer similar to the wireless device 222.

As shown, the locomotive 600 may also include an on-board control system 610. The control system 610 can control the tractive efforts and/or braking efforts of the locomotive 600 and, optionally, other locomotives that are directly or indirectly coupled to the locomotive 600. Operations of the control system 610 may be based on inputs received from an operator of the locomotive and/or remote inputs from, for example, a control tower, a dispatch facility, or the like. In addition, the control system 610 may receive inputs from various components of the locomotive 600. In some cases, the inputs may be data signals received through wireless communication. For example, the wireless devices of the gear cases 602, the engine 604, the turbo-charger 606, and the air compressor 608 may be configured to wirelessly communicate data signals to the control system 610. The control system 610 may include a reader 612 for receiving the wireless data signals. The control system 610 may also include a signal-processing module and a planning module that are similar to the signal-processing and planning modules 120, 122 described in FIG. 1. The planning module may generate operating plans for the locomotive 600 based on the inputs received.

Figure 15:
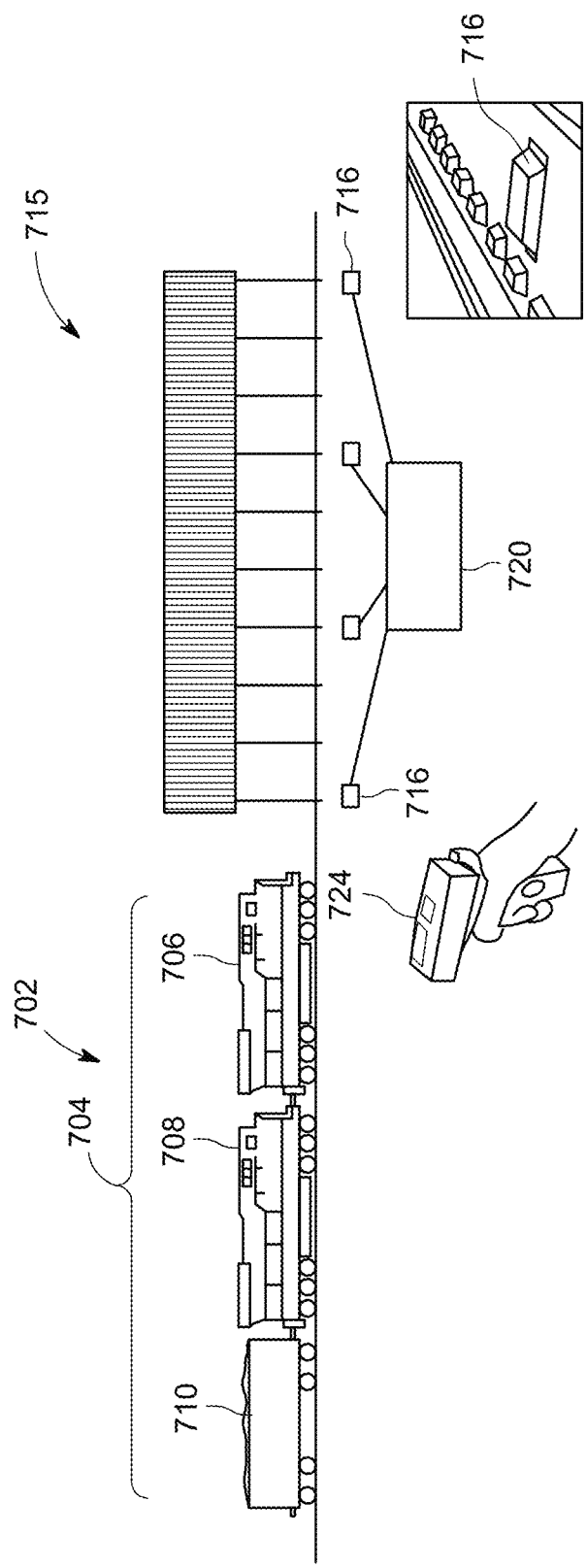
FIG. 15 illustrates a system in accordance with an embodiment for obtaining data signals from one or more wireless devices.
Figure 16:
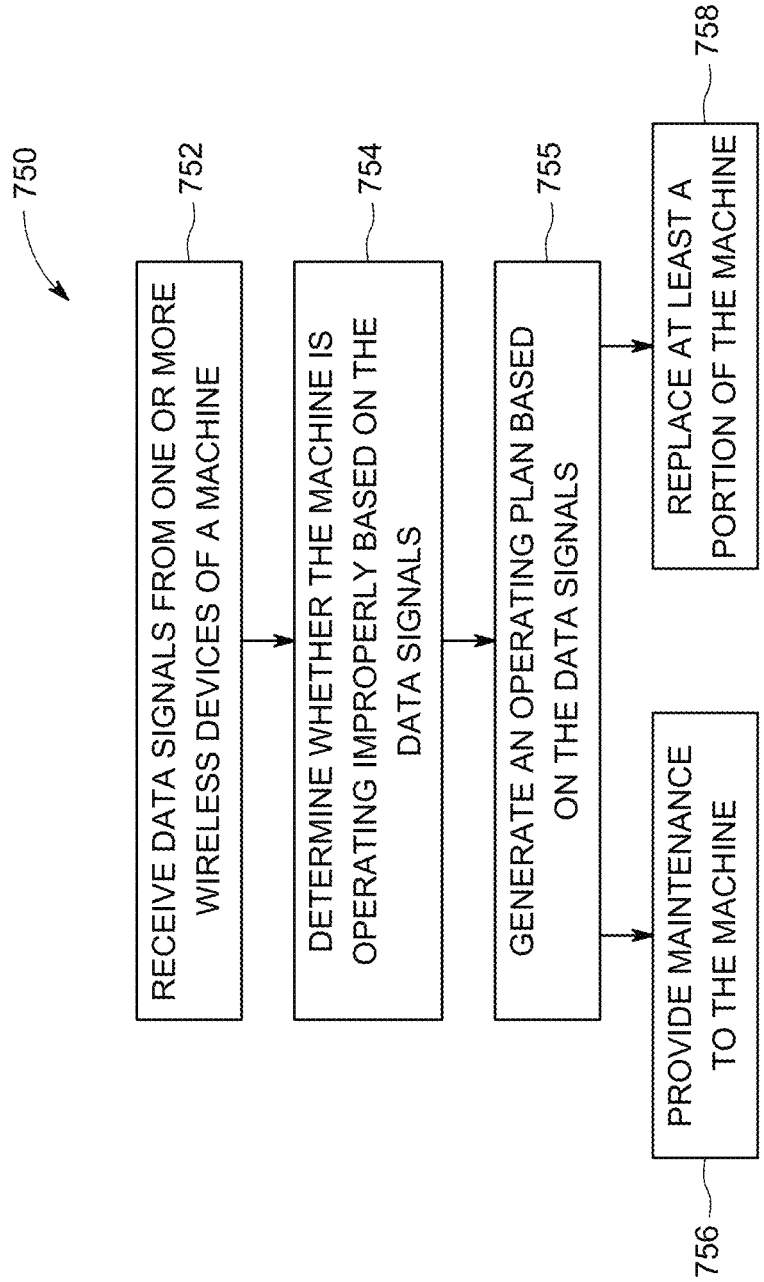
FIG. 16 is a flowchart illustrating a method in accordance with an embodiment.

FIG. 15 illustrates a system 700 in accordance with one embodiment for obtaining data signals from one or more wireless devices. FIG. 16 illustrates a flowchart of a method 750 that may be executed or performed by the system 700. In some embodiments, the locomotive 600 (FIG. 14) may also execute or perform the method 750. The system 700 and the method 750 may employ structures or aspects of various embodiments discussed herein. In some embodiments, certain steps of the method 750 may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Likewise, the system 700 is not required to include each and every feature of each and every embodiment described herein.

With respect to FIG. 15, the system 700 includes a vehicle system 702 (e.g., train) including a locomotive consist 704. The locomotive consist 704 may include at least one locomotive that is linked (directly or indirectly) to one or more rail cars. For example, FIG. 15 shows the locomotive consist 704 including first and second locomotives 706, 708 and a rail car 710. In other embodiments, the vehicle system 702 may include more rail cars 710. Each of the locomotives 706 and 708 may include a plurality of components that are each monitored by one or more wireless devices. For example, each of the locomotives 706, 708 may include an engine, a turbo-charger, an air compressor, and a plurality of gear cases, such as those described herein.

As shown in FIG. 15, the vehicle system 702 is approaching a designated reading location 715. The reading location 715 is a maintenance facility in the illustrated embodiment. However, the reading location 715 may be a variety of other locations that are capable of receiving wireless data signals from the locomotives. For example, the reading location 715 may be a depot, fuel station, wayside location, rail yard entry point or exit point, designated sections of the track(s), and the like. The reading location 715 includes a plurality of readers 716. Each of the readers 716 is communicatively coupled (e.g., wirelessly or through communication wires) to a control system 720. Alternatively or additionally, a handheld reader 724 may be carried by an individual and used to receive the data signals. The reader 724 may also communicate data signals with the control system 720.

The control system 720 may include a signal-processing module and a planning module, such as the signal-processing and planning modules 120, 122 described in FIG. 1. For example, the control system 720 may generate operating plans that include instructions for operating the vehicle system 702 and other similar vehicle systems.

The method 750 may include receiving (at 752) data signals from one or more of the wireless devices of a machine. In the illustrated embodiment, the machine is the vehicle system 702 or one of the locomotives 704, 706. However, embodiments described herein are not necessarily limited to locomotives. The machine may have one or components with moving mechanical elements or parts. For example, the machine may have a drive train, engine, air compressor, and/or turbo-charger. The data signals may be representative of a measurement of an operative condition of the component. By way of example the measurement may be at least one of a vibration measurement, a capacitance of a liquid, a temperature of a liquid, a fluid conduction of a liquid, a dielectric constant of a liquid, an impedance of a liquid, or a viscosity of a liquid. In particular embodiments, the measurement is representative of a vibratory state of a gear case or of a liquid condition of a lubricant held in the gear case.

The receiving operation (at 752) may include receiving the data signals at one or more fixed readers having stationary positions. For example, the readers 716 may have fixed positions with respect to tracks 730. The readers 716 may be located at designated distance from the tracks 730 so that the readers 716 are capable of receiving the data signals. The receiving operation (at 752) may also include receiving the data signals through one or more movable readers, such as the handheld reader 724.

In an alternative embodiment, as described above, the receiving operation (at 752) may occur with an on-board control system, such as the control system 610 (FIG. 14).

The method 750 also included determining (at 754), based on the data signals, whether the component of the machine is operating improperly. For example, the control system 720 may analyze the data signals and, optionally, other inputs to determine whether the component is operating sufficiently. If the component is operating improperly, the method 750 also includes generating (at 755) an operating plan that is based on the data signals. The operating plan may be a new (or revised) operating plan that is configured to replace a currently-implemented operating plan. The method 750 may also include at least one of providing maintenance (at 756) to the component or replacing (at 758) an element of the component.

In an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In one aspect, the transmitter is configured to be energized by the reader when the reader interrogates the transmitter.

In one aspect, the system includes a power source that is configured to supply power to the transmitter for transmitting the data signals. The power source may include, for example, a battery and/or energy harvesting device.

In one aspect, the sensor is configured to be at least partially submerged in the liquid.

In one aspect, the measurement is at least one of a capacitance of the liquid, a temperature of the liquid, a fluid conduction of the liquid, a dielectric constant of the liquid, an impedance of the liquid, or a viscosity of the liquid.

In one aspect, the device body is configured to be affixed to a wall of the machine in which the wall at least partially defines the reservoir.

In one aspect, the sensor and the device body collectively form a first wireless device. The system may also include a second wireless device that is configured to obtain and wirelessly communicate second data signals that are representative of a measurement of a different reservoir.

In one aspect, the sensor is configured to be disposed in a gear case of a locomotive, the gear case having the reservoir.

In one aspect, the transmitter is included in a radio-frequency identification (RFID) element.

In one aspect, the sensor, the processing unit, and the transmitter collectively form a first wireless device. The system may also include a second wireless device that is configured to obtain and wirelessly transmit data signals that are representative of a measurement of a different reservoir. The system may include a signal-processing module. The signal-processing module may be configured to determine, based on the data signals, whether the machine is operating improperly by comparing the data signals of the first wireless device to the data signals of the second wireless device.

In one aspect, the data signals are configured to be transmitted to a handheld reader. In another aspect, the data signals are configured to be transmitted to a fixed reader located along a railway track. In yet another aspect, the data signals are configured to be transmitted to an on-board reader located on a locomotive.

In one aspect, the sensor includes a multi-conductor capacitive sensor configured to detect a capacitance of a fluid. The fluid may function as a dielectric, wherein a level of the fluid affects the capacitance detected. In another aspect, the sensor includes a body float and a position transducer configured to detect a position of the body float. The position transducer may include, for example, a reed switch.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In one aspect, the system includes a power source configured to supply power to the transmitter for transmitting the data signals.

In one aspect, the system includes a memory. The memory is configured to log a plurality of the measurements obtained at different times. The transmitter is configured to transmit data signals that include the measurements.

In one aspect, the sensor, the processing unit, and the transmitter collectively form a first wireless device. The system may include a second wireless device configured to obtain and wirelessly transmit data signals that are based on a measurement of a different drive train.

In one aspect, the device body includes a radio-frequency identification (RFID) unit. The RFID unit may have the processing unit and the transmitter.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In one aspect, the measurement is representative of vibratory state of a gear case or a liquid condition of a lubricant held in the gear case.

In one aspect, the measurement is at least one of a vibration measurement of a gear case, a capacitance of a lubricant stored by the gear case, a temperature of the lubricant, a fluid conduction of the lubricant, a dielectric constant of the lubricant, impedance of the lubricant, or a viscosity of the lubricant.

In one aspect, the data signals are received from a plurality of wireless devices. The data signals are based on a common type of measurement.

In one aspect, the data signals are received at a handheld reader.

In one aspect, the machine is a locomotive and the data signals are received at a fixed reader located along a railway track.

In one aspect, the machine is a locomotive and the data signals are received at a reader located on-board the locomotive.

In one aspect, the method also includes operating the machine according to a first operating plan and generating a second operating plan that is based on the operative condition.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

In another embodiment, a system (e.g., wireless liquid monitoring system) comprises a sensor, a processing unit, and a transmitter. The sensor is configured to be disposed within a reservoir of a machine having moving parts that are lubricated by a liquid in the reservoir. The sensor is configured to obtain a measurement of the liquid that is representative of at least one of a quantity or quality of the liquid in the reservoir. The processing unit is operably coupled to the sensor and configured to generate first data signals representative of the measurement of the liquid. The transmitter is operably coupled to the processing unit and configured to wirelessly communicate the first data signals to a remote reader.

In another embodiment of the system, alternatively or additionally, the transmitter is an RFID unit, which may be, for example, similar to an RFID tag, chip, card, or label.

In another embodiment of the system, alternatively or additionally, the system is configured to be disposed in the machine (and when installed is actually disposed in the machine), which comprises a vehicle or other powered system comprising the reservoir, the moving parts, and one or more computers or other controller-based units (e.g., a vehicle controller) other than the processing unit. The system may not be physically electrically connected (e.g., not connected by wires or other conductors) to any of the one or more computers or other controller-based units in the machine. Thus, the first data signals may only wirelessly transmitted from the system to the reader or elsewhere, and are not transmitted via wire/cables or other physical electrical connections.

In another embodiment of the system, alternatively or additionally, the processing unit and transmitter are co-located proximate to one another (e.g., at least partially integrated onto a common circuit board, positioned within a common box/housing that is positioned within the machine—that is, the common box/housing is not coextensive with the outer body/structure of the machine, but is located within the outer body/structure—and/or some or all of the components of the processing unit and transmitter are located within 10 cm of each other, within 5 cm of each other, etc., for example), and/or at least portions of the processing unit and transmitter are directly connected to a wall of the reservoir (e.g., a wall that bears a pressure of and/or contacts the liquid in the reservoir) and/or to a structure immediately connected to such a wall (e.g., support structure of the reservoir, gear case, or the like).

In another embodiment of the system, alternatively or additionally, the transmitter is configured to wirelessly communicate the first data signals to the remote reader that comprises: a remote reader located within the machine (e.g., if the machine is a vehicle, the remote reader is located with the vehicle); a remote reader located on a wayside of a route of the machine, the machine comprising a vehicle; a portable (handheld, or otherwise able to be carried by a human operator) remote reader.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system," "module," or "controller" may include hardware and/or software that operate(s) to perform one or more functions. For example, a system, module, or controller may include a computer processor or other logic-based device that performs operations based on instructions stored on a tangible and non-transitory computer readable storage medium, such as a computer memory. Alternatively, a system, module, or controller may include a hard-wired device that performs operations based on hard-wired logic of the device. The systems, modules, and controllers shown in the Figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
a sensor sized to be disposed within a reservoir of a machine having moving parts that are lubricated by a liquid in the reservoir, the sensor configured to obtain a measurement of the liquid that is representative of at least one of a quantity or quality of the liquid in the reservoir; and
a device body operably coupled to the sensor, the device body including a processing unit-and a transmitter, the device body configured to wirelessly receive an interrogation signal from a remote reader, the interrogation signal including electric energy that energizes the processing unit to generate a data signal representative of the measurement of the liquid obtained by the sensor, the electric energy of the interrogation signal additionally energizing the transmitter to wirelessly communicate the data signal to the remote reader;
wherein the device body is configured to be mounted to a wall of the machine, the wall at least partially defining the reservoir, the device body further including an accelerometer operably coupled to the processing unit and configured to obtain a vibration measurement of the wall, the processing unit configured to determine that the machine is in a stationary state based on the vibration measurement indicating less than a threshold amount of vibration of the wall for a designated amount of time, the processing unit configured to generate the data signal representative of the measurement of the liquid for communication by the transmitter during the stationary state of the machine.

2. The system of claim 1, wherein the sensor is configured to obtain the measurement of the liquid responsive to receiving a query from the processing unit requesting the measurement, the processing unit configured to communicate the query to the sensor responsive to receiving the interrogation signal.

3. The system of claim 1, further comprising a power source configured to supply power to the transmitter for communicating the data signal.

4. The system of claim 1, wherein the sensor is configured to be at least partially submerged in the liquid.

5. The system of claim 1, wherein the measurement is at least one of a fluid level, a temperature of the liquid or nearby components, a fluid conduction of the liquid, a dielectric constant of the liquid, an impedance of the liquid, or a viscosity of the liquid.

6. The system of claim 1, wherein the machine is a vehicle and the reservoir is in a gear case of the vehicle.

7. The system of claim 1, wherein the device body is configured to be affixed to a wall of the machine, the wall at least partially defining the reservoir.

8. The system of claim 1, wherein the remote reader comprises at least one of a handheld reader, a fixed reader located along a railway track, or an on-board reader located on a rail vehicle.

9. The system of claim 1, wherein the sensor comprises a multi-conductor capacitive sensor configured to detect a capacitance of the liquid, the liquid functioning as a dielectric, wherein a level of the liquid affects the capacitance detected.

10. The system of claim 1, wherein the sensor comprises a body float and a position transducer configured to detect a position of the body float.

11. The system of claim 1, wherein the sensor communicates the measurement of the liquid to the processing unit as an analog signal, the processing unit including an analog-to-digital converter that converts the analog signal to a digital signal to generate the data signal.

12. The system of claim 1, wherein the processing unit is configured to determine that the machine is in an active state based on the vibration measurement from the accelerometer indicating greater than the threshold amount of vibration of the wall, the processing unit configured to not generate the data signal representative of the measurement of the liquid during the active state of the machine.

13. The system of claim 1, wherein the sensor is a capacitive sensor configured to be disposed in contact with the liquid to obtain a capacitance measurement of the liquid, the system further comprising a temperature sensor operably coupled to the device body and disposed in contact with the liquid to obtain a temperature measurement of the liquid, the device body mounted to a wall of the reservoir and spaced apart from the liquid in the reservoir, the capacitive sensor and the temperature sensor operably coupled to the device body via corresponding wires.

14. The system of claim 1, further comprising a cable portion extending between the sensor and the device body, the cable portion configured to extend through a port of a wall of the machine, wherein the wall at least partially defines the reservoir, the cable portion extending between a first end outside of the reservoir that is secured to the device body and a second end inside the reservoir that is secured to the sensor, the cable portion housing one or more wires extending between the sensor and the device body to electrically connect the sensor to the device body.

15. The system of claim 14, wherein the cable portion defines a fill channel that provides fluid access to the reservoir from outside of the wall.

16. A method comprising:
providing a device body mounted to a wall of a machine having moving parts, the machine including a reservoir at least partially defined by the wall, the moving parts lubricated by a liquid in the reservoir, the device body including a processing unit, a transmitter, and an accelerometer operably coupled to the processing unit, the accelerometer configured to obtain a vibration measurement of the wall, the processing unit configured to determine that the machine is in a stationary state based on the vibration measurement indicating less than a threshold amount of vibration of the wall for a designated amount of time;
receiving, at the device body, a measurement of the liquid in the reservoir representative of at least one of a quantity or a quality of the liquid in the reservoir, the measurement obtained from a sensor disposed within the reservoir;
wirelessly receiving, at the device body, an interrogation signal from a remote reader;
generating, by the processing unit, a data signal representative of the measurement of the liquid obtained by the sensor, the processing unit generating the data signal using electric energy of the interrogation signal, the processing unit generating the data signal only during a stationary state of the machine; and
wirelessly communicating, by the transmitter, the data signal to the remote reader, the transmitter wirelessly communicating the data signal using the electric energy of the interrogation signal.

17. The method of claim 16, further comprising communicating a query to the sensor to obtain the measurement of the liquid responsive to receiving the interrogation signal.

18. A system comprising:
a sensor sized to be disposed within a reservoir of a machine having moving parts that are lubricated by a liquid in the reservoir, the sensor configured to obtain a measurement of the liquid that is representative of at least one of a quantity or quality of the liquid in the reservoir; and
a device body operably coupled to the sensor, the device body including a processing unit and a transmitter, the processing unit configured to communicate a query to the sensor requesting the sensor to obtain the measurement of the liquid responsive to receiving an interrogation signal from a remote reader, the processing unit further configured to generate a data signal representative of the measurement of the liquid obtained by the sensor, the transmitter configured to wirelessly communicate the data signal to the remote reader;
wherein the device body is configured to be mounted to a wall of the machine, the wall at least partially defining the reservoir, the device body further including an accelerometer operably coupled to the processing unit and configured to obtain a vibration measurement of the wall, the processing the unit configured to determine that the machine is in a stationary state based on the vibration measurement indicating less than a threshold amount of vibration of the wall for a designated amount of time, the processing unit configured to generate the data signal representative of the measurement of the liquid for communication by the transmitter during the stationary state of the machine.

19. The system of claim 18, wherein the transmitter is configured to use electric energy of the interrogation signal to energize the transmitter to wirelessly communicate the data signal to the remote reader.

* * * * *